(12) United States Patent
Fry et al.

(10) Patent No.: US 9,457,093 B2
(45) Date of Patent: Oct. 4, 2016

(54) SOLID DISPERSIONS OF A ERB2 (HER2) INHIBITOR

(71) Applicant: Array BioPharma Inc., Boulder, CO (US)

(72) Inventors: David Shank Fry, Boulder, CO (US); Christopher M. Lindemann, Boulder, CO (US); Michael Preigh, Boulder, CO (US); Corey Jay Bloom, Boulder, CO (US); Christopher Donovan Craig, Boulder, CO (US); Devon Brevard Dubose, Boulder, CO (US); Jeff Gautschi, Boulder, CO (US); Dan Smithey, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 14/351,840

(22) PCT Filed: Oct. 12, 2012

(86) PCT No.: PCT/US2012/060044
§ 371 (c)(1),
(2) Date: Apr. 14, 2014

(87) PCT Pub. No.: WO2013/056108
PCT Pub. Date: Apr. 18, 2013

(65) Prior Publication Data
US 2014/0296267 A1    Oct. 2, 2014

Related U.S. Application Data

(60) Provisional application No. 61/547,620, filed on Oct. 14, 2011, provisional application No. 61/606,207, filed on Mar. 2, 2012.

(51) Int. Cl.
| | |
|---|---|
| *A61K 47/38* | (2006.01) |
| *A61K 31/517* | (2006.01) |
| *A61K 47/32* | (2006.01) |
| *A61K 9/10* | (2006.01) |
| *A61K 9/20* | (2006.01) |
| *A61K 9/16* | (2006.01) |

(52) U.S. Cl.
CPC .............. *A61K 47/38* (2013.01); *A61K 9/10* (2013.01); *A61K 9/1635* (2013.01); *A61K 9/1652* (2013.01); *A61K 9/2009* (2013.01); *A61K 9/2027* (2013.01); *A61K 9/2054* (2013.01); *A61K 9/2077* (2013.01); *A61K 31/517* (2013.01); *A61K 47/32* (2013.01)

(58) Field of Classification Search
CPC ............ A61K 9/2009; A61K 9/2027; A61K 9/2954; A61K 9/1635; A61K 47/38; A61K 9/2077; A61K 31/517; A61K 9/10; A61K 47/32

See application file for complete search history.

(56) References Cited

U.S. PATENT DOCUMENTS

| | | | |
|---|---|---|---|
| 7,452,895 B2 | 11/2008 | Wallace et al. | |
| 7,501,427 B2 | 3/2009 | Wallace et al. | |
| 7,585,975 B2 | 9/2009 | Wallace et al. | |
| 7,777,032 B2 | 8/2010 | Wallace et al. | |
| 8,278,314 B2 | 10/2012 | Wallace et al. | |
| 8,648,087 B2 | 2/2014 | Lyssikatos et al. | |
| 2004/0058956 A1* | 3/2004 | Akiyama et al. | 514/318 |
| 2013/0245256 A1 | 9/2013 | Wallace et al. | |
| 2014/0023643 A1 | 1/2014 | Lyssikatos et al. | |

(Continued)

FOREIGN PATENT DOCUMENTS

| | | |
|---|---|---|
| JP | 200095708 A | 4/2000 |
| JP | 2010526848 A | 8/2010 |

(Continued)

OTHER PUBLICATIONS fda.gov. "Background Information for the Oct. 2002 ACPS Meeting Scientific Considerations of Polymorphism in Pharmaceutical Solids: Abbreviated New Drug Applications." Retrieved on Oct. 6, 2015. Retrieved from the Internet <URL: http://www.fda.gov/ohrms/dockets/ac/02/briefing/3900B1_04_Polymorphism.htm>.*

(Continued)

*Primary Examiner* — Anoop Singh
*Assistant Examiner* — Doan Phan
(74) *Attorney, Agent, or Firm* — Viksnins Harris & Padys PLLP; Corey M. Williams

(57) ABSTRACT

A solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and processes for preparing the solid dispersion are provided herein. Also, a pharmaceutical composition comprising a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and uses thereof are provided herein.

(I)

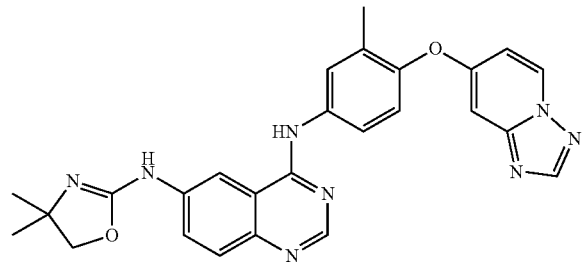

24 Claims, 13 Drawing Sheets

(56) References Cited

U.S. PATENT DOCUMENTS

2014/0243361 A1   8/2014   Corson et al.
2015/0110780 A1   4/2015   Lee et al.

FOREIGN PATENT DOCUMENTS

| WO | 2005026152 A1 | | 3/2005 | |
|---|---|---|---|---|
| WO | 20050261151 A1 | | 3/2005 | |
| WO | WO 2007059257 A2 | * | 5/2007 | |
| WO | WO 2009042618 A1 | * | 4/2009 | |
| WO | WO 2009135799 A2 | * | 11/2009 | ............ G01N 33/15 |
| WO | WO 2010023187 A1 | * | 3/2010 | |

OTHER PUBLICATIONS

MedKo Biosciences. "Irbinitinib (ARRY-380)." Retrieved on Oct. 6, 2015. Retrieved from the Internet <URL: http://www.medkoo.com/Anticancer-trials/ARRY-380.htm>.*

Friesen et al., "Hydroxypropyl Methylcellulose Acetate Succinate-Based Spray-Dried Dispersions: An Overview", Molecular Pharmaceutics vol. 5 (6), 1003-1019 (2008).

Koch, "ARRY-380: A Selective, Oral HER2 inhibitor for the Treatment of Solid Tumors"XP002692140, http://www.arraybiopharma.com/_documents/Publication/PubAttachment462.pdf, 29 pages (2011).

Leuner et al., "Improving drug solubility for oral delivery using solid dispersions", European Journal of Pharmaceutics and Biopharmaceutics 50, 47-60 (2000).

Lindemann et al. "Amorphous Dispersion Development of ARRY-380, an ErbB2 Selective Inhibitor." American Association of Pharmaceutical Scientists, Annual Meeting and Exposition. Oct. 17, 2012.

Lindemann et al. "Solid-State Characterization of Seven Isomorphic Solvates of ARRY-380." American Association of Pharmaceutical Scientists, Annual Meeting and Exposition. Oct. 17, 2012.

Okamoto, "PSWC2004 Symposium Report on Pharmaceutical Field", Pharm Tech Japan 8, vol. 20 (9), 1783-1785 (2004). [English Translation].

Patent Cooperation Treaty, International Searching Authority, Search Report and Written Opinion for PCT/US2012/060044, 16 pages, May 16, 2013.

Tiwari et al., "Solid Dispersions: An Overview to Modify Bioavailability of Poorly Water Soluble Drugs", International Journal of PharmTech Research, vol. 1 (4), 1338-1349 (2009).

Vasconcelos et al., "Solid dispersions as strategy to improve oral bioavailability of poor water soluble drugs", Drug Discovery Today, vol. 12 (23-24), 1068-1075 (2007).

Ansel, Howard C., et al. Pharmaceutical Dosage Forms and Drug Delivery Systems. p. 91. Philadelphia: Lippincott Williams & Wilkins, 7th Edition 1999.

Chia, S.K.L. et al. "A Phase 1 Study to Assess the Safety, Tolerability and PK of ARRY-380—an Oral Inhibitor of ErbB2." San Antonio Breast Cancer Symposium, Dec. 9-13, 2009.

Dinkel, Victoria, et al. "ARRY-380, a potent, small molecule inhibitor of ErbB2, increases survival in intracranial ErbB2+ xenograft models in mice." American Association for Cancer Research, Apr. 1, 2012.

Lee, Patrice, et al. "In Vivo Activity of ARRY-380, a Potent, Small Molecule Inhibitor of ErbB2 in Combination with Trastuzumab, Docetaxel or Bevacizumab." San Antonio Breast Cancer Symposium, Dec. 9-13, 2009.

Lee, Patrice, et al. "In Vivo Activity of ARRY-380, a Potent, Small Molecule Inhibitor of ErbB2 in Combination with Trastuzumab or Docetaxel in BT-474 Human Breast Carcinoma Xenograft Model." Association for Cancer Research, Apr. 18-22, 2009.

Morrow, PK, et al. "A Phase 1 Study to Assess the Safety, Tolerability and PK of ARRY-380—an Oral Inhibitor of HER2." American Society of Clinical Oncologists, Oct. 1, 2010.

Moulder, S.L., et al. "ARRY-380, a Selective HER2 Inhibitor: From Drug Design to Clinical Evaluation." AACR-NCI-EORTC International Conference: Molecular Targets and Cancer Therapeutics, Nov. 14, 2011.

Moulder, SL, et al. "Data from a Completed Phase 1 Study to Assess the Safety, Tolerability and PK of ARRY-380—an Oral Inhibitor of HER2." San Antonio Breast Cancer Symposium, Dec. 10, 2010.

Pheneger, Tracy, et al. "In Vitro and In Vivo Activity of ARRY-380: a Potent, Small Molecule Inhibitor of ErbB2." American Association for Cancer Research, Apr. 18-22, 2009.

Iqbal, et al., "Recent advances and patents in solid dispersion technology", Recent Pat Drug Deliv Formul. 5 (3), 244-264 (2011).

* cited by examiner

SOLID DISPERSIONS OF A ERB2 (HER2) INHIBITOR

RELATED APPLICATIONS

This application claims priority to U. S. Provisional Application No. 61/547,620 that was filed on Oct. 14, 2011, and U. S. Provisional Application No. 61/606,207that was filed on Mar. 2, 2012. The entire content of these provisional applications are hereby incorporated herein by reference.

BACKGROUND OF THE INVENTION

1. Field of the Invention

A solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine is provided herein. Also, a pharmaceutical composition comprising a solid dispersion of N4-(4-([1,2,4]triazolo[1,5-60 ]pyridin-7-yloxy)-3-methylphenyl)-N6-(4,4-dimethyl-4,5dihydrooxazol -2-yl)quinazoline-4,6-diamine is provided herein.

2. Description of the State of the Art

N4-(4-([1,2,4]Triazolo[1,5-60 ]pyridin-7-yloxy)-3-methylphenyl)-N6-(4,4-dimethyl-4,5-dihydrooxazol-2-yl)quinazoline-4,6-diamine (also called "ARRY-380"), which has the structure:

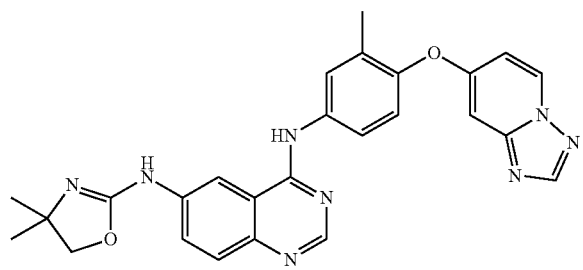 [SMILES: Cc1cc(Nc2ncnc3ccc(NC4=NC(C)(C)CO4)cc23)ccc1Oc1ccn2ncnc2c1]

is a selective ErbB2 (HER2) inhibitor described in WO 2007/059257, which is incorporated by reference in its entirety. N4-(4-([1,2,4]Triazolo[1,5-α]pyridin-7-yloxy)-3-methylphenyl)-N6-(4,4-dimethyl-4,5-dihydrooxazol-2-yl)quinazoline-4,6-diamine has been tested in human clinical trials for hyperproliferative diseases, particularly cancer (see Koch, Kevin. "ARRY-380: A Selective, Oral HER2Inhibitor for the Treatment of Solid Tumors." American Association of Cancer Research 102nd Annual Meeting, Apr. 3, 2011; which may also be found at: http://www.arraybiopharma.com/_documents/Publication/PubAttachment462.pdf).

A powder-in-capsule ("PIC") composition of N4-(4-([1, 2,4]triazolo[1,5-α]pyridin-7-yloxy)-3-methylphenyl)-N6-(4,4-dimethyl-4,5-dihydrooxazol-2-yl)quinazoline-4,6-diamine was prepared and administerred to patients with cancer, and the overall inter-patient variability for area under the plasma concentration-time curve ("AUC") and maximum concentration ("Cmax") was moderate to high.

There remains a need to prepare a pharmaceutical composition containing N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine that minimizes inter-patient variability of pharmacokinetics.

SUMMARY OF THE INVENTION

A solid dispersion comprising N4-(4-([1,2,4]triazolo[1,5-60 ]pyridin-7-yloxy)-3-methylphenyl)-N6-(4,4-dimethyl-4,5-dihydrooxazol-2-yl)quinazoline-4,6-diamine is described herein.

A pharmaceutical composition comprising N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine is described herein.

A pharmaceutical composition comprising a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine is described herein.

A pharmaceutical composition comprising a solid dispersion of spray dried N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine is described herein.

Processes for preparing the solid dispersion and pharmaceutical composition and methods of using the pharmaceutical composition are also described herein.

DETAILED DESCRIPTION OF THE INVENTION

Figure 1:
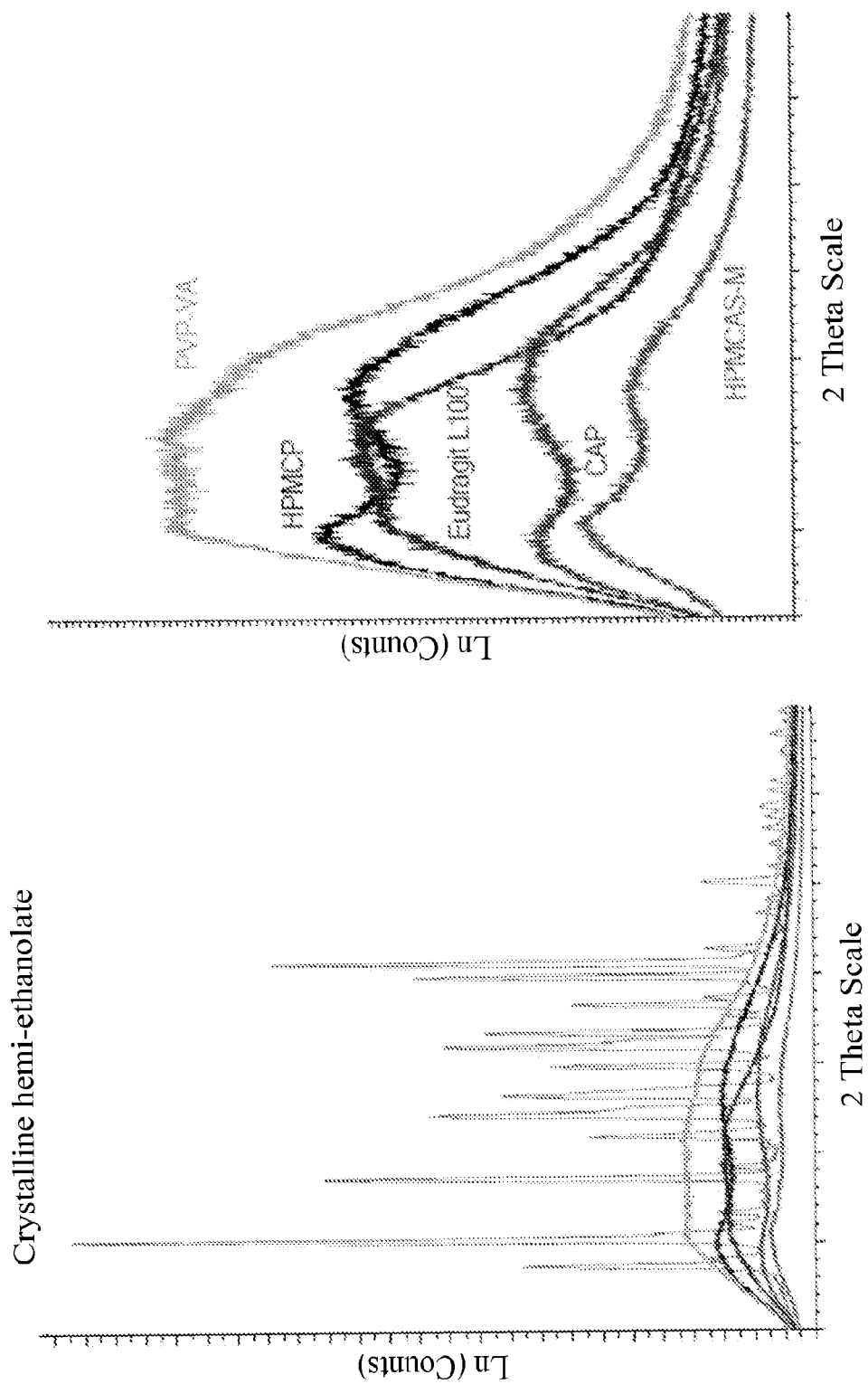
FIG. 1 shows a comparison of XRPD scans of amorphous 30% solid dispersions and crystalline N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine, with a close up of the amorphous solid dispersions.

Reference will now be made in detail to certain embodiments, examples of which are illustrated herein. While enumerated embodiments will be described, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2, can be 0, 1 or 2 for variables that are inherently discrete, and can be 0.0, 0.1, 0.01, 0.001, or any other real value for variables that are inherently continuous.

The term "amorphous" means a solid in a solid state that is a non-crystalline state. Amorphous solids generally possess crystal-like short range molecular arrangement, but no long range order of molecular packing as found in crystalline solids. The solid state form of a solid may be determined by polarized light microscopy, x-ray powder diffraction ("XRPD"), differential scanning calorimetry ("DSC"), or other standard techniques known to those of skill in the art.

The phrase "amorphous solid dispersion" means a solid comprising a drug substance and a dispersion polymer. The amorphous solid dispersion discussed herein comprises amorphous N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and a dispersion polymer, wherein the amorphous solid dispersion contains N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in a substantially amorphous solid state form. In certain embodiments, the substantially amorphous solid state form means that the N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine component in the amorphous solid dispersion is at least 80% amorphous N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine. In certain embodiments, the substantially amorphous solid state form means that the N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine component in the amorphous solid dispersion is at least 85% amorphous N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine. In certain embodiments, the substantially amorphous solid state form means that the N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine component in the amorphous solid dispersion is at least 90% amorphous N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine. In certain embodiments, the substantially amorphous solid state form means that the N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine component in the amorphous solid dispersion is at least 95% amorphous N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

The terms "cancer" and "cancerous" refer to or describe the physiological condition in mammals that is typically characterized by abnormal or unregulated cell growth.

A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, brain, endometrial or uterine carcinoma, salivary gland carcinoma, kidney or renal cancer, prostate cancer, vulval cancer, thyroid cancer, hepatic carcinoma, anal carcinoma, penile carcinoma, skin cancer, including melanoma, as well as head and neck cancer.

The phrase "dispersion polymer" means a polymer that allows for N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine to be dispersed throughout such that a solid dispersion may form. The dispersion polymer is preferably neutral or basic. The dispersion polymer may contain a mixture of two or more polymers. Examples of dispersion polymers include, but are not limited to, vinyl polymers and copolymers, vinylpyrrolidine vinylacetate copolymer ("PVP-VA"), polyvinyl alcohols, polyvinyl alcohol polyvinyl acetate copolymers, polyvinyl pyrrolidine ("PVP"), acrylate and methacrylate copolymers, methylacrylic acid methyl methacrylate copolymer (such as Eudragit®), polyethylene polyvinyl alcohol copolymers, polyoxyethylene-polyoxypropylene block copolymers (also referred to as poloxamers), graft copolymer comprised of polyethylene glycol, polyvinyl caprolactam and polyvinyl acetate (such as Soluplus®), cellulosic polymers, such as hydroxypropyl methyl cellulose acetate ("HPMCA"), hydroxypropyl methyl cellulose ("HPMC"), hydroxypropyl cellulose ("HPC"), methyl cellulose, hydroxyethyl methyl cellulose, hydroxyethyl cellulose, hydroxyethyl cellulose acetate, and hydroxyethyl ethyl cellulose, hydroxypropyl methyl cellulose acetate succinate ("HPMCAS"), hydroxypropyl methyl cellulose phthalate ("HPMCP"), carboxymethylethyl cellulose ("CMEC"), cellulose acetate phthalate ("CAP"), cellulose acetate succinate ("CAS"), hydroxypropyl methyl cellulose acetate phthalate ("HPMCAP"), cellulose acetate trimellitate ("CAT"), hydroxypropyl methyl cellulose acetate trimellitate ("HPMCAT"), and carboxymethylcellulose acetate butyrate ("CMCAB"), and the like.

The term "mammal" means a warm-blooded animal that has or is at risk of developing a disease described herein and includes, but is not limited to, guinea pigs, dogs, cats, rats, mice, hamsters, and primates, including humans.

The phrase "pharmaceutically acceptable" indicates that the substance or composition is compatible chemically and/or toxicologically, with the other ingredients comprising a composition, and/or the mammal being treated therewith.

The phrase "pharmaceutically acceptable salt," as used herein, refers to pharmaceutically acceptable organic or inorganic salts of a compound described herein.

The phrase "solid dispersion" means a system in a solid state comprising at least two components, wherein one component is dispersed throughout the other component. The solid dispersion discussed herein comprises one component of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine dispersed throughout another component, particularly a dispersion polymer.

The phrase "spray drying" means processes involved in breaking up liquid mixtures into small droplets (atomization) and rapidly removing solvent from the mixture in a spray drying apparatus where there is a strong driving force for evaporation of solvent from the droplets. The phrase spray drying is used conventionally and broadly. Spray drying processes and spray drying equipment are described generally in Perry, Robert H., and Don W. Green (eds.). *Perry's Chemical Engineers' Handbook*. New York: McGraw-Hill, 2007 (8$^{th}$ edition).

The phrases "therapeutically effective amount" or "effective amount" mean an amount of a compound described herein that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "treat" or "treatment" refer to therapeutic, prophylactic, palliative or preventative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

Solid Dispersions and Pharmaceutical Compositions

Provided herein is a solid dispersion comprising N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

The solid dispersions are generally prepared by dissolving the drug substance and the dispersion polymer in a suitable solvent to form a feed solution, and then the feed solution may be spray dried to form the solid dispersion (and remove the solvent). Spray drying is a known process. Spray drying is generally performed by dissolving N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and the dispersion polymer in a suitable solvent to prepare a feed solution. The feed solution may be pumped through an atomizer into a drying chamber. The feed solution can be atomized by conventional means known in the art, such as a two-fluid sonicating nozzle, a pressure nozzle, a rotating nozzle and a two-fluid non-sonicating nozzle. Then, the solvent is removed in the drying chamber to form the solid dispersion. A typical drying chamber uses hot gases, such as forced air, nitrogen, nitrogen-enriched air, or argon to dry particles. The size of the drying chamber may be adjusted to achieve particle properties or throughput.

Although the solid dispersion are preferably prepared by conventional spray drying techniques, other techniques known in the art may be used, such as melt extrusion, freeze drying, rotary evaporation, drum drying or other solvent removal processes.

In one embodiment, a process of preparing a solid dispersion is provided, comprising:

(a) dissolving N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and a dispersion polymer in a suitable solvent; and (b) evaporating the solvent to form the solid dispersion. In a further embodiment, the evaporation of the solvent in step (b) is performed by spray drying, melt extrusion, freeze drying, rotary evaporation, drum drying or other solvent removal processes.

In certain embodiments, the dispersion polymer is selected from PVP-VA, methylacrylic acid methyl methacrylate copolymer, HPMCP, CAP, HPMCAS and HPMC and mixtures thereof. In certain embodiments, the dispersion polymer is selected from PVP-VA, methylacrylic acid methyl methacrylate copolymer, HPMCP, CAP, HPMCAS and HPMC. In certain embodiments, the dispersion polymer is selected from PVP-VA, Eudragit® L100, HPMCP H-55, CAP, HPMCAS Grade M, HPMC and mixtures thereof. In certain embodiments, the dispersion polymer is selected from PVP-VA, Eudragit® L100, HPMCP H-55, CAP, HPMCAS Grade M and HPMC.

In certain embodiments, the dispersion polymer is selected from PVP-VA, methylacrylic acid methyl methacrylate copolymer, HPMCP, CAP and HPMCAS, and mixtures thereof. In certain embodiments, the dispersion polymer is selected from PVP-VA, methylacrylic acid methyl methacrylate copolymer, HPMCP, CAP and HPMCAS. In certain embodiments, the dispersion polymer is selected from PVP-VA, Eudragit® L100, HPMCP H-55, CAP and HPMCAS Grade M, and mixtures thereof. In certain embodiments, the dispersion polymer is selected from PVP-VA, Eudragit® L100, HPMCP H-55, CAP and HPMCAS Grade M.

In certain embodiments, the dispersion polymer is selected from PVP-VA, methylacrylic acid methyl methacrylate copolymer, HPMCP, CAP and HPMC, and mixtures thereof. In certain embodiments, the dispersion polymer is selected from PVP-VA, methylacrylic acid methyl methacrylate copolymer, HPMCP, CAP and HPMC. In certain embodiments, the dispersion polymer is selected from PVP-VA, Eudragit® L100, HPMCP H-55, CAP and HPMC, and mixtures thereof. In certain embodiments, the dispersion polymer is selected from PVP-VA, Eudragit® L100, HPMCP H-55, CAP and HPMC.

In certain embodiments, the dispersion polymer is selected from PVP-VA, methylacrylic acid methyl methacrylate copolymer, HPMCP and CAP, and mixtures thereof. In certain embodiments, the dispersion polymer is selected from PVP-VA, methylacrylic acid methyl methacrylate copolymer, HPMCP and CAP. In certain embodiments, the dispersion polymer is selected from PVP-VA, Eudragit® L100, HPMCP H-55 and CAP, and mixtures thereof. In certain embodiments, the dispersion polymer is selected from PVP-VA, Eudragit® L100, HPMCP H-55 and CAP.

In certain embodiments, the dispersion polymer is PVP-VA.

In certain embodiments, the dispersion polymer is methylacrylic acid methyl methacrylate copolymer. In certain embodiments, the dispersion polymer is Eudragit®. In certain embodiments, the dispersion polymer is Eudragit® L100.

In certain embodiments, the dispersion polymer is HPMCP. In certain embodiments, the dispersion polymer is HPMCP H-55.

In certain embodiments, the dispersion polymer is CAP.

In certain embodiments, the dispersion polymer is HPMCAS. In certain embodiments, the dispersion polymer is HPMCAS Grade M.

In certain embodiments, the dispersion polymer is preferably neutral or basic.

In certain embodiments, the dispersion polymer is selected from PVP-VA and HPMC. In certain embodiments, the dispersion polymer is HPMC.

Suitable solvents are a solvent or mixture of solvents in which both N4-(4-([1,2,4]triazolo[1,5α]pyridin-7-yloxy)-3-methylphenyl)-N6-(4,4-dimethyl-4,5-dihydrooxazol-2-yl)quinazoline-4,6-diamine and the dispersion polymer have adequate solubility (solubility greater than 1 mg/mL). A mixture of solvents may be used if each component of the solid dispersion (i.e., N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and dispersion polymer) require different solvents to obtain the desired solubility. The solvent may be volatile with a boiling point of 150° C. or less. In addition, the solvent should have relatively low toxicity and be removed from the dispersion to a level that is acceptable to The International Committee on Harmonization ("ICH") guidelines. Removal of solvent to this level may require a subsequent processing step, such as tray drying. Examples of suitable solvents include, but are not limited to, alcohols, such as methanol ("MeOH"), ethanol ("EtOH"), n-propanol, isopropanol ("IPA") and butanol; ketones, such as acetone, methyl ethyl ketone ("MEK") and methyl isobutyl ketone; esters, such as ethyl acetate ("EA") and propyl acetate; and various other solvents, such as tetrahydrofuran ("THF"), acetonitrile ("ACN"), methylene chloride, toluene and 1,1,1-trichloroethane. Lower volatility solvents, such as dimethyl acetate or dimethylsulfoxide ("DMSO"), may be used. Mixtures of solvents with water may also be used, so long as the polymer and N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine are sufficiently soluble to make the spray drying process practicable. Generally, due to the hydrophobic nature of low solubility drugs, non-aqueous solvents may be used, meaning the solvent comprises less than about 10 weight % water.

In certain embodiments, the suitable solvent is selected from MeOH and THF, and mixtures thereof. In certain embodiments, the suitable solvent is MeOH:THF solvent system of about 1:3. In certain embodiments, the suitable solvent is a 1:3 MeOH:THF solvent system.

In certain embodiments, the suitable solvent is selected from MeOH, THF and water, and mixtures thereof. In certain embodiments, the suitable solvent is selected from MeOH, THF and water. In certain embodiments, the suitable solvent is a THF:MeOH:water solvent system of about 80:10:10. In certain embodiments, the suitable solvent is a 80:10:10 THF:MeOH:water solvent system. In certain embodiments, the suitable solvent is a THF:MeOH:water solvent system of about 82:8:10. In certain embodiments, the suitable solvent is a 82:8:10 THF:MeOH:water solvent system. In certain embodiments, the suitable solvent is a THF:MeOH:water solvent system of about 82.2:8.2:9.6. In certain embodiments, the suitable solvent is a 82.2:8.2:9.6 THF:MeOH:water solvent system.

In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion ranges from about 0.1% to about 70% by weight relative to the dispersion polymer. In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion ranges from 0.1% to 70% by weight relative to the dispersion polymer.

In certain embodiments, the amount of N4-(4-([1,2,4]triazolo[1,5-60 ]pyridin-7-yloxy)-3-methylphenyl)-N6-(4,4-dimethyl-4,5-dihydrooxazol-2-yl)quinazoline-4,6-diamine in the solid dispersion ranges from about 1% to about 60% by weight relative to the dispersion polymer. In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion ranges from 1% to 60% by weight relative to the dispersion polymer.

In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion ranges from about 5% to about 60% by weight relative to the dispersion polymer. In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion ranges from 5% to 60% by weight relative to the dispersion polymer.

In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion ranges from about 55% to about 65% by weight relative to the dispersion polymer. In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion ranges from 55% to 65% by weight relative to the dispersion polymer. In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion is about 60% by weight relative to the dispersion polymer. In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion is 60% by weight relative to the dispersion polymer.

In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion ranges from about 25% to about 35% by weight relative to the dispersion polymer. In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion ranges from 25% to 35% by weight relative to the dispersion polymer. In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion is about 30% by weight relative to the dispersion polymer. In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion is 30% by weight relative to the dispersion polymer.

In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion ranges from about 45% to about 55% by weight relative to the dispersion polymer. In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion ranges from 45% to 55% by weight relative to the dispersion polymer. In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion is about 50% by weight relative to the dispersion polymer. In certain embodiments, the amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine in the solid dispersion is 50% by weight relative to the dispersion polymer.

In certain embodiments, the solid dispersion is an amorphous solid dispersion.

Another embodiment provides a pharmaceutical composition comprising a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and a dispersion polymer, and a carrier or excipient.

Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005.

The pharmaceutical compositions may also include one or more additional components, such as buffers, dispersion agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug, i.e., a compound described herein or pharmaceutical composition thereof, or aid in the manufacturing of the pharmaceutical product, i.e., medicament (see Ansel; Gennaro; and Rowe above). The components of the pharmaceutical composition should be pharmaceutically acceptable.

Certain embodiments provide a pharmaceutical composition comprising:
(a) about 1 to about 70 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) about 0.1 to about 20 weight % of a disintegrant;
(c) about 0.1 to about 25 weight % of an osmogen;
(d) about 0.1 to about 10 weight % of a glidant;
(e) about 0.1 to about 10 weight % of a lubricant; and
(f) about 0.1 to about 25 weight % of a binder/diluent.

In a further embodiment, the pharmaceutical composition comprises:
(a) 1 to 70 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) 0.1 to 20 weight % of a disintegrant;
(c) 0.1 to 25 weight % of an osmogen;
(d) 0.1 to 10 weight % of a glidant;
(e) 0.1 to 10 weight % of a lubricant; and
(f) 0.1 to 25 weight % of a binder/diluent.

Certain embodiments provide a pharmaceutical composition comprising:
(a) about 25 to about 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) about 5 to about 15 weight % of a disintegrant;
(c) about 15 to about 25 weight % of an osmogen;
(d) about 0.1 to about 3 weight % of a glidant;
(e) about 0.1 to about 3 weight % of a lubricant; and
(f) about 10 to about 25 weight % of a binder/diluent.

In a further embodiment, the pharmaceutical composition comprises:
(a) 25 to 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) 5 to 15 weight % of a disintegrant;
(c) 15 to 25 weight % of an osmogen;
(d) 0.1 to 3 weight % of a glidant;
(e) 0.1 to 3 weight % of a lubricant; and
(f) 10 to 25 weight % of a binder/diluent.

Certain embodiments provide a pharmaceutical composition comprising:
(a) about 40 to about 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) about 5 to about 15 weight % of a disintegrant;
(c) about 15 to about 25 weight % of an osmogen;
(d) about 0.1 to about 3 weight % of a glidant;
(e) about 0.1 to about 3 weight % of a lubricant; and
(f) about 10 to about 25 weight % of a binder/diluent.

In a further embodiment, the pharmaceutical composition comprises:
(a) 40 to 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;

(b) 5 to 15 weight % of a disintegrant;
(c) 15 to 25 weight % of an osmogen;
(d) 0.1 to 3 weight % of a glidant;
(e) 0.1 to 3 weight % of a lubricant; and
(f) 10 to 25 weight % of a binder/diluent.

Certain embodiments provide a pharmaceutical composition comprising:
(a) about 1 to about 70 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) about 0.1 to about 20 weight % of a disintegrant;
(c) about 0.1 to about 25 weight % of an osmogen;
(d) about 0.1 to about 10 weight % of a glidant;
(e) about 0.1 to about 10 weight % of a lubricant; and
(f) about 0.1 to about 25 weight % of a filler.

In a further embodiment, the pharmaceutical composition comprises:
(a) 1 to 70 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) 0.1 to 20 weight % of a disintegrant;
(c) 0.1 to 25 weight % of an osmogen;
(d) 0.1 to 10 weight % of a glidant;
(e) 0.1 to 10 weight % of a lubricant; and
(f) 0.1 to 25 weight % of a filler.

Certain embodiments provide a pharmaceutical composition comprising:
(a) about 25 to about 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) about 1 to about 10 weight % of a disintegrant;
(c) about 15 to about 25 weight % of an osmogen;
(d) about 0.1 to about 3 weight % of a glidant;
(e) about 0.1 to about 3 weight % of a lubricant; and
(f) about 10 to about 25 weight % of a filler.

In a further embodiment, the pharmaceutical composition comprises:
(a) 25 to 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) 1 to 10 weight % of a disintegrant;
(c) 15 to 25 weight % of an osmogen;
(d) 0.1 to 3 weight % of a glidant;
(e) 0.1 to 3 weight % of a lubricant; and
(f) 10 to 25 weight % of a filler.

Certain embodiments provide a pharmaceutical composition comprising:
(a) about 40 to about 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) about 1 to about 10 weight % of a disintegrant;
(c) about 15 to about 25 weight % of an osmogen;
(d) about 0.1 to about 3 weight % of a glidant;
(e) about 0.1 to about 3 weight % of a lubricant; and
(f) about 10 to about 25 weight % of a filler.

In a further embodiment, the pharmaceutical composition comprises:
(a) 40 to 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) 1 to 10 weight % of a disintegrant;
(c) 15 to 25 weight % of an osmogen;
(d) 0.1 to 3 weight % of a glidant;
(e) 0.1 to 3 weight % of a lubricant; and
(f) 10 to 25 weight % of a filler.

In certain embodiments, the osmogen is selected from NaCl and KCl, and mixtures thereof.

In certain embodiments, the lubricant is magnesium stearate.

In certain embodiments, the glidant is colloidal silicon dioxide.

In certain embodiments, the binder/diluent is microcrystalline cellulose. In certain embodiments, the binder/diluent acts as both a binder and a diluent.

In certain embodiments, the binder is microcrystalline cellulose.

In certain embodiments, the diluent is microcrystalline cellulose.

In certain embodiments, the filler is lactose.

In certain embodiments, the disintegrant is selected from crospovidone and sodium bicarbonate (NaHCO$_3$), and mixtures thereof. In certain embodiments, the disintegrant is selected from crospovidone and sodium bicarbonate. In certain embodiments, the disintegrant is sodium bicarbonate. In certain embodiments, the disintegrant is crospovidone.

In certain embodiments, the composition contains sodium bicarbonate. N4-(4-([1,2,4]Triazolo[1,5-α]pyridin-7-yloxy)-3-methylphenyl)-N6-(4,4-dimethyl-4,5-dihydrooxazol-2-yl)quinazoline-4,6-diamine may slowly degrade, through hydrolysis or other means, to a carbamate impurity:

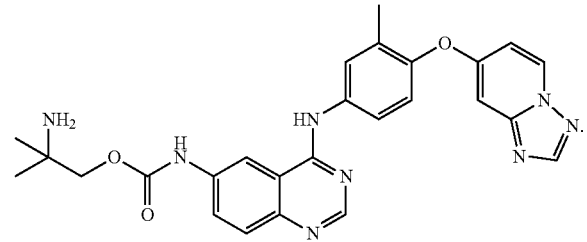 [SMILES: Cc1cc(Nc2ncnc3ccc(NC(=O)OCC(C)(C)N)cc23)ccc1Oc1ccn2ncnc2c1]

Sodium bicarbonate helps to slow the degradation to the carbamate impurity. Sodium bicarbonate also helps to provide consistent tablet disintegration when the tablets are exposed to different humidities.

Certain embodiments provide a pharmaceutical composition comprising:
(a) N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine; and
(b) sodium bicarbonate.

Certain embodiments provide a pharmaceutical composition comprising:
(a) about 1 to about 70 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine; and
(b) about 0.1 to about 30 weight % sodium bicarbonate.

In a further embodiment, the pharmaceutical composition comprises:
(a) 1 to 70 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine; and
(b) 0.1 to 30 weight % sodium bicarbonate.

Certain embodiments provide a pharmaceutical composition comprising:
(a) about 1 to about 70 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) about 0.1 to about 30 weight % sodium bicarbonate; and
(c) the remaining weight is other pharmaceutically acceptable excipients and carriers.

In a further embodiment, the pharmaceutical composition comprises:
(a) 1 to 70 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) 0.1 to 30 weight % sodium bicarbonate; and
(c) the remaining weight is other pharmaceutically acceptable excipients and carriers.

Certain embodiments provide a pharmaceutical composition comprising:
(a) about 25 to about 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine; and
(b) about 1 to about 15 weight % of sodium bicarbonate.

In a further embodiment, the pharmaceutical composition comprises:
(a) 25 to 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine; and
(b) 1 to 15 weight % of sodium bicarbonate.

Certain embodiments provide a pharmaceutical composition comprising:
(a) about 25 to about 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) about 1 to about 15 weight % of sodium bicarbonate; and
(c) the remaining weight is other pharmaceutically acceptable excipients and carriers.

In a further embodiment, the pharmaceutical composition comprises:
(a) 25 to 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) 1 to 15 weight % of sodium bicarbonate; and
(c) the remaining weight is other pharmaceutically acceptable excipients and carriers.

Certain embodiments provide a pharmaceutical composition comprising:
(a) about 40 to about 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine; and
(b) about 1 to about 15 weight % of sodium bicarbonate.

In a further embodiment, the pharmaceutical composition comprises:
(a) 40 to 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine; and
(b) 1 to 15 weight % of sodium bicarbonate.

Certain embodiments provide a pharmaceutical composition comprising:
(a) about 40 to about 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) about 1 to about 15 weight % of sodium bicarbonate;
(c) the remaining weight is other pharmaceutically acceptable excipients and carriers.

In a further embodiment, the pharmaceutical composition comprises:
(a) 40 to 60 weight % of a solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine;
(b) 1 to 15 weight % of sodium bicarbonate;
(c) the remaining weight is other pharmaceutically acceptable excipients and carriers.

The pharmaceutical composition preferably contains a therapeutically effective amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine. However, in some embodiments, each individual dose contains a portion of a therapeutically effective amount of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine, such that multiple doses of the composition may be required (for example, two or more tablets are required for a therapeutically effective amount). Thus, in this application when it states that the pharmaceutical composition contains a therapeutically effective amount it means that the composition may be one dose (for example, one tablet) or multiple doses (for example, two tablets). In certain embodiments, the pharmaceutical composition contains between 1 and 500 mg of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

In certain embodiments, the pharmaceutical composition contains between 25 and 400 mg of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

In certain embodiments, the pharmaceutical composition contains between 100 and 300 mg of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

The pharmaceutical compositions described herein may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), ocular, vaginal, intraperitoneal, intrapulmonary and intranasal. If parenteral administration is desired, the compositions will be sterile and in a solution or suspension form suitable for injection or infusion.

The compounds may be administered in any convenient administrative form, e.g., tablets, powders, capsules, dispersions, suspensions, syrups, sprays, suppositories, gels, emulsions, patches, etc.

The pharmaceutical compositions described herein are typically administered orally. The pharmaceutical compositions described herein are typically administered as a tablet, caplet, hard or soft gelatin capsule, pill, granules or a suspension.

Methods of Treatment with Compounds of the Invention

Also provided are methods of treating or preventing disease or condition by administering the pharmaceutical composition described herein. In one embodiment, a human patient is treated with a pharmaceutical composition described herein in an amount to inhibit ErbB2 activity. In one embodiment, a human patient is treated with a pharmaceutical composition described herein in an amount to detectably inhibit ErbB2 activity.

In another embodiment, a method of treating a hyperproliferative disease in a mammal comprising administering the pharmaceutical composition described herein, to the mammal is provided.

In certain embodiments, the hyperproliferative disease is cancer.

In another embodiment, a method of treating or preventing cancer in a mammal in need of such treatment, wherein the method comprises administering to said mammal a pharmaceutical composition described herein. The cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, NSCLC, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia. Another embodiment provides the use of a pharmaceutical composition described herein, in the manufacture of a medicament for the treatment of cancer.

In another embodiment, the cancer is ErbB2 positive.

In another embodiment, the cancer is selected from breast, gastric, biliary, colorectal, lung, NSCLC, pancreatic, head and neck, ovarian, uterine and brain cancer.

In another embodiment, the cancer is selected from breast, gastric, biliary, colorectal, lung, NSCLC, pancreatic, head and neck, ovarian and uterine cancer.

In another embodiment, the cancer is selected from breast, gastric, colorectal, lung and ovarian cancer.

In another embodiment, the cancer is selected from breast, ovarian, gastric and uterine cancer.

In another embodiment, the cancer is selected from breast, gastric, colorectal, NSCLC and ovarian cancer.

In another embodiment, the cancer is selected from breast, lung, pancreatic, colorectal and head and neck cancers.

In another embodiment, the cancer is breast cancer.
In another embodiment, the cancer is gastric cancer.
In another embodiment, the cancer is biliary cancer.
In another embodiment, the cancer is colorectal cancer.
In another embodiment, the cancer is lung cancer.
In another embodiment, the cancer is NSCLC.
In another embodiment, the cancer is pancreatic cancer.
In another embodiment, the cancer is head and neck cancer.
In another embodiment, the cancer is ovarian cancer.
In another embodiment, the cancer is uterine cancer.
In another embodiment, the cancer is brain cancer.

In another embodiment, a method of treating or preventing a disease or disorder modulated by ErbB2, comprising administering to a mammal in need of such treatment an effective amount of a pharmaceutical composition described herein. Examples of such diseases and disorders include, but are not limited to, cancer.

Another embodiment provides the use of a pharmaceutical composition described herein, in the manufacture of a medicament for the treatment of cancer.

Another embodiment provides the solid dispersions described herein for the treatment of disease. In a further embodiment, the disease is a hyperproliferative disease. In a further embodiment, the hyperproliferative disease is cancer.

Another embodiment provides the pharmaceutical compositions described herein for the treatment of disease. In a further embodiment, the disease is a hyperproliferative disease. In a further embodiment, the hyperproliferative disease is cancer.

EXAMPLES

For illustrative purposes, the following Examples are included. However, it is to be understood that these Examples do not limit the invention and are only meant to suggest a method of practicing the invention. Persons skilled in the art will recognize that the chemical reactions described may be readily adapted to prepare the compounds described herein, and alternative methods for preparing the compounds are deemed to be within the scope of this invention. For example, the synthesis of the compounds described herein may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing the compounds described herein. Persons skilled in the art will also recognize that the solid dispersions and compositions described may be readily adapted to prepare other dispersions and compositions, and alternative methods for preparing the dispersions and compositions, as well as alternative compositions are deemed to be within the scope of this invention.

Example 1

30% Solid Dispersion using PVP-VA

A solid dispersion was prepared containing 30 weight percent N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and PVP-VA using a Buchi B-290 mini spray drier. The solid dispersion was spray dried from a MeOH:THF (1:3) solvent system, a 5% spray solution concentration, an inlet temperature of 100° C. at a flow rate of 22 mL/minute, drying gas flow rate of 35 $m^3$/hour, nozzle pressure of 80 psig, nozzle gas flow of 0.66 $m^3$/hour, and a 1.5 mm nozzle type. Secondary drying of the dispersion was done at 40° C. under vacuum for about 16 hours. The spray drying yielded 19.6 g (87.7% yield) of the solid dispersion. Physicochemical analysis results are in Table 1. The XRPD scan is shown in FIG. 1. Residual solvent analysis showed that the dispersion had less than 0.5% THF and no detectable MeOH.

Figure 2:
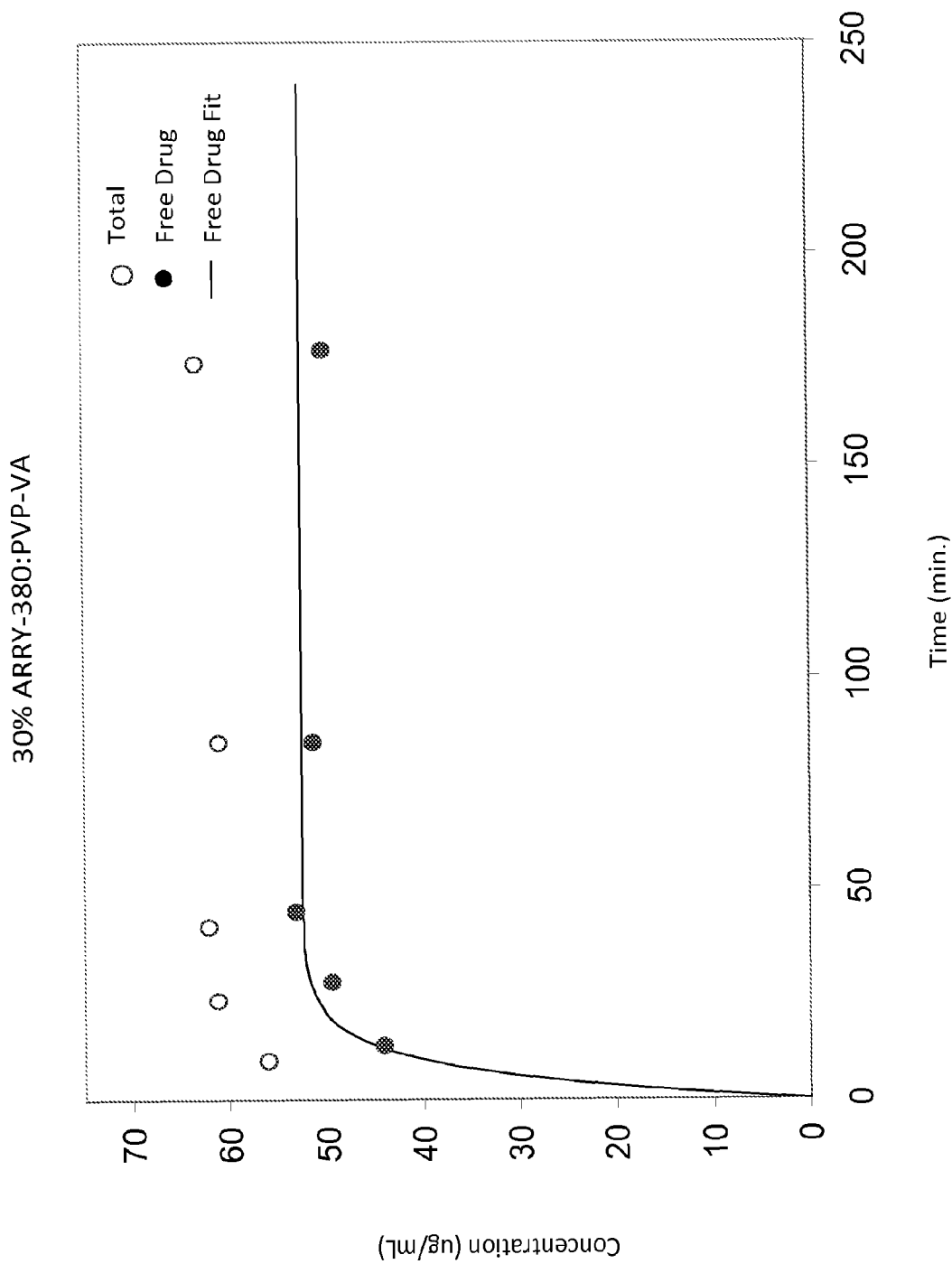
FIG. 2 shows a dissolution profile of a 30% solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

Dissolution testing was performed at a pH of 6.5 in phosphate buffer. The solid dispersion was suspended in $H_2O$ and added directly to the buffer solution at 37° C. The dissolution profile was collected over a period of about 240 minutes. The results are in FIG. 2. The Cmax and AUC for the total drug species (colloidal+free) was 63.46 µg/mL and 245.05 μg/mL*hr, respectively. The Cmax and AUC for the free drug species was 52.50 μg/mL and 204.12 μg/mL*hr, respectively.

Example 2

30% Solid Dispersion using Eudragit

A solid dispersion was prepared containing 30 weight percent N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and Eudragit L100 using a Buchi B-290 mini spray drier. The solid dispersion was spray dried from a MeOH:THF (1:3) solvent system, a 5% spray solution concentration, an inlet temperature of 100° C. at a flow rate of 22 mL/minute, drying gas flow rate of 35 m$^3$/hour, nozzle pressure of 80 psig, nozzle gas flow of 0.66 m$^3$/hour, and a 1.5 mm nozzle type. Secondary drying of the dispersion was done at 40° C. under vacuum for about 16 hours. The spray drying yielded 18.6 g (82.7% yield) of the solid dispersion. Physicochemical analysis results are in Table 1. The XRPD scan is shown in FIG. 1. Residual solvent analysis showed that the dispersion had about 4.5% THF and no detectable MeOH.

Figure 3:
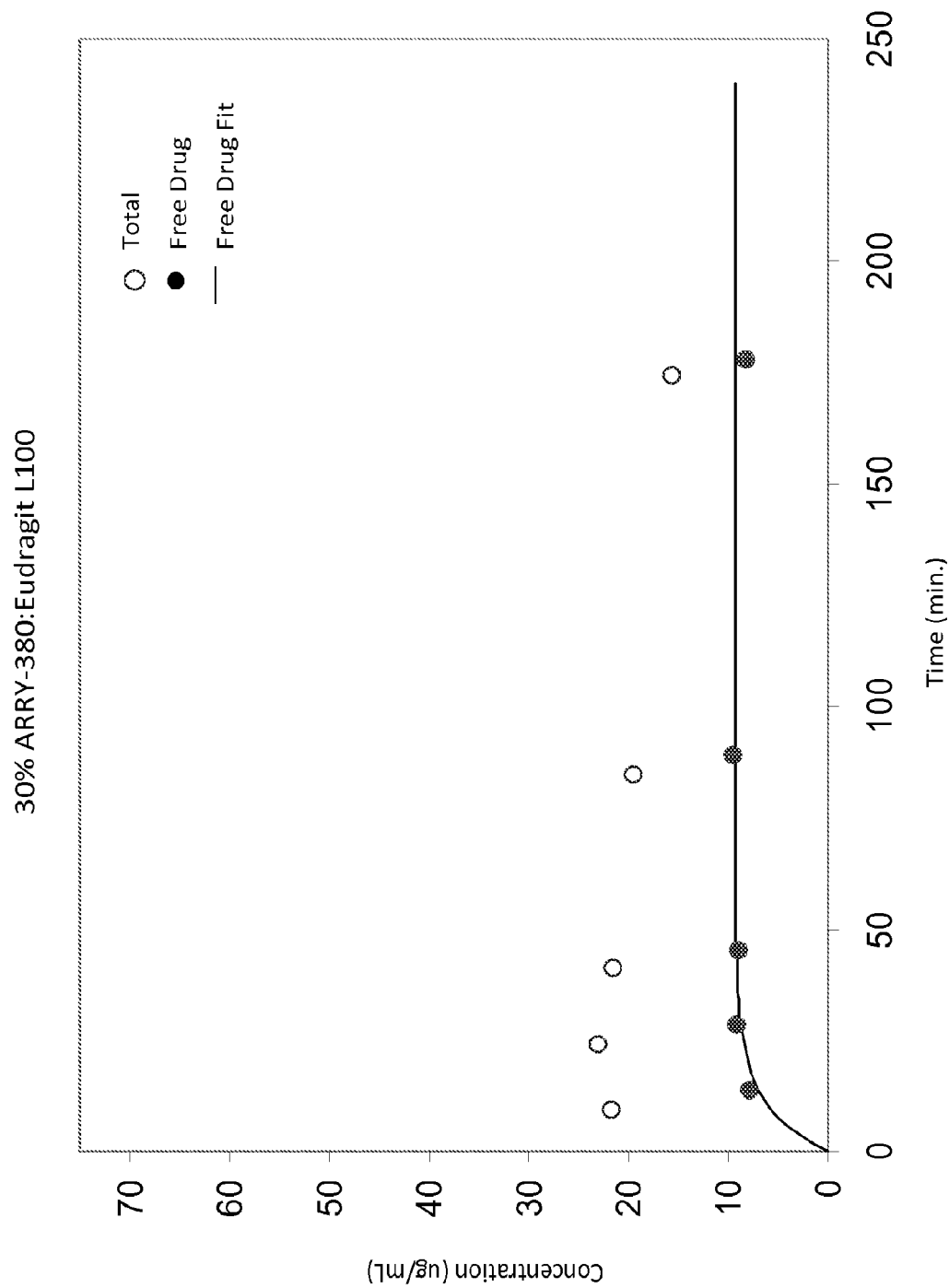
FIG. 3 shows a dissolution profile of a 30% solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

Dissolution testing was performed at a pH of 6.5 in phosphate buffer. The solid dispersion was suspended in H$_2$O and added directly to the buffer solution at 37° C. The dissolution profile was collected over a period of about 240 minutes. The results are in FIG. 3. The Cmax and AUC for the total drug species (colloidal+free) was 22.70 μg/mL and 71.06 μg/mL*hr, respectively. The Cmax and AUC for the free drug species was 9.26 μg/mL and 35.49 μg/mL*hr, respectively.

Example 3

30% Solid Dispersion using HPMCP

A solid dispersion was prepared containing 30 weight percent N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and HPMCP H-55 using a Buchi B-290 mini spray drier. The solid dispersion was spray dried from a MeOH:THF (1:3) solvent system, a 5% spray solution concentration, an inlet temperature of 100° C. at a flow rate of 22 mL/minute, drying gas flow rate of 35 m$^3$/hour, nozzle pressure of 80 psig, nozzle gas flow of 0.66 m$^3$/hour, and a 1.5 mm nozzle type. Secondary drying of the dispersion was done at 40° C. under vacuum for about 16 hours. The spray drying yielded 20.3 g (90.3% yield) of the solid dispersion. Physicochemical analysis results are in Table 1. The XRPD scan is shown in FIG. 1. Residual solvent analysis showed that the dispersion had less than 0.5% THF and no detectable MeOH.

Figure 4:
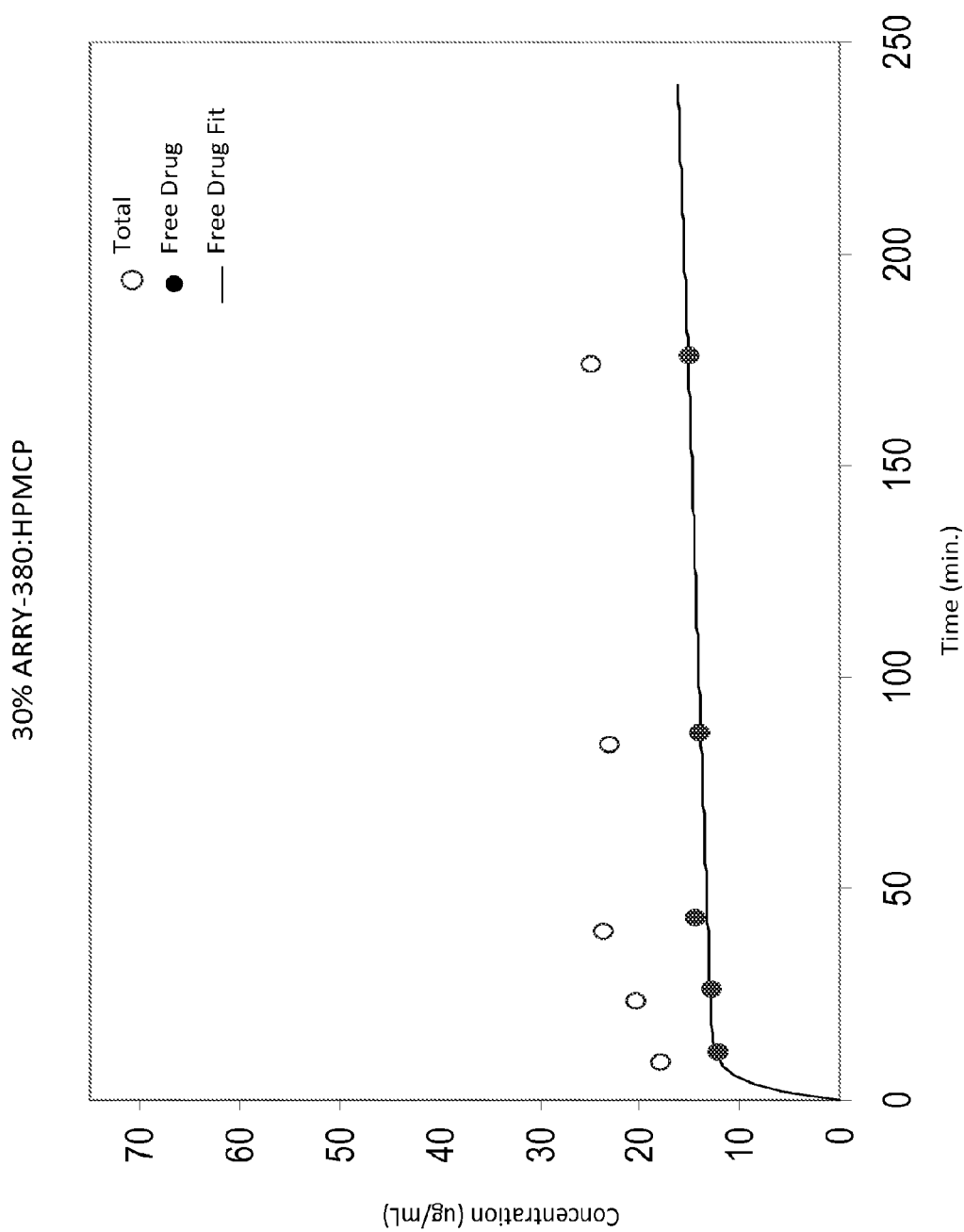
FIG. 4 shows a dissolution profile of a 30% solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

Dissolution testing was performed at a pH of 6.5 in phosphate buffer. The solid dispersion was suspended in H$_2$O and added directly to the buffer solution at 37° C. The dissolution profile was collected over a period of about 240 minutes. The results are in FIG. 4. The Cmax and AUC for the total drug species (colloidal+free) was 25.00 μg/mL and 96.66 μg/mL*hr, respectively. The Cmax and AUC for the free drug species was 16.15 μg/mL and 56.81 μg/mL*hr, respectively.

Example 4

30% Solid Dispersion using CAP

A solid dispersion was prepared containing 30 weight percent N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and CAP using a Buchi B-290 mini spray drier. The solid dispersion was spray dried from a MeOH:THF (1:3) solvent system, a 5% spray solution concentration, an inlet temperature of 100° C. at a flow rate of 22 mL/minute, drying gas flow rate of 35 m$^3$/hour, nozzle pressure of 80 psig, nozzle gas flow of 0.66 m$^3$/hour, and a 1.5 mm nozzle type. Secondary drying of the dispersion was done at 40° C. under vacuum for about 16 hours. The spray drying yielded 20.0 g (90.4% yield) of the solid dispersion. Physicochemical analysis results are in Table 1. The XRPD scan is shown in FIG. 1. Residual solvent analysis showed that the dispersion had less than 0.5% THF and no detectable MeOH.

Figure 5:
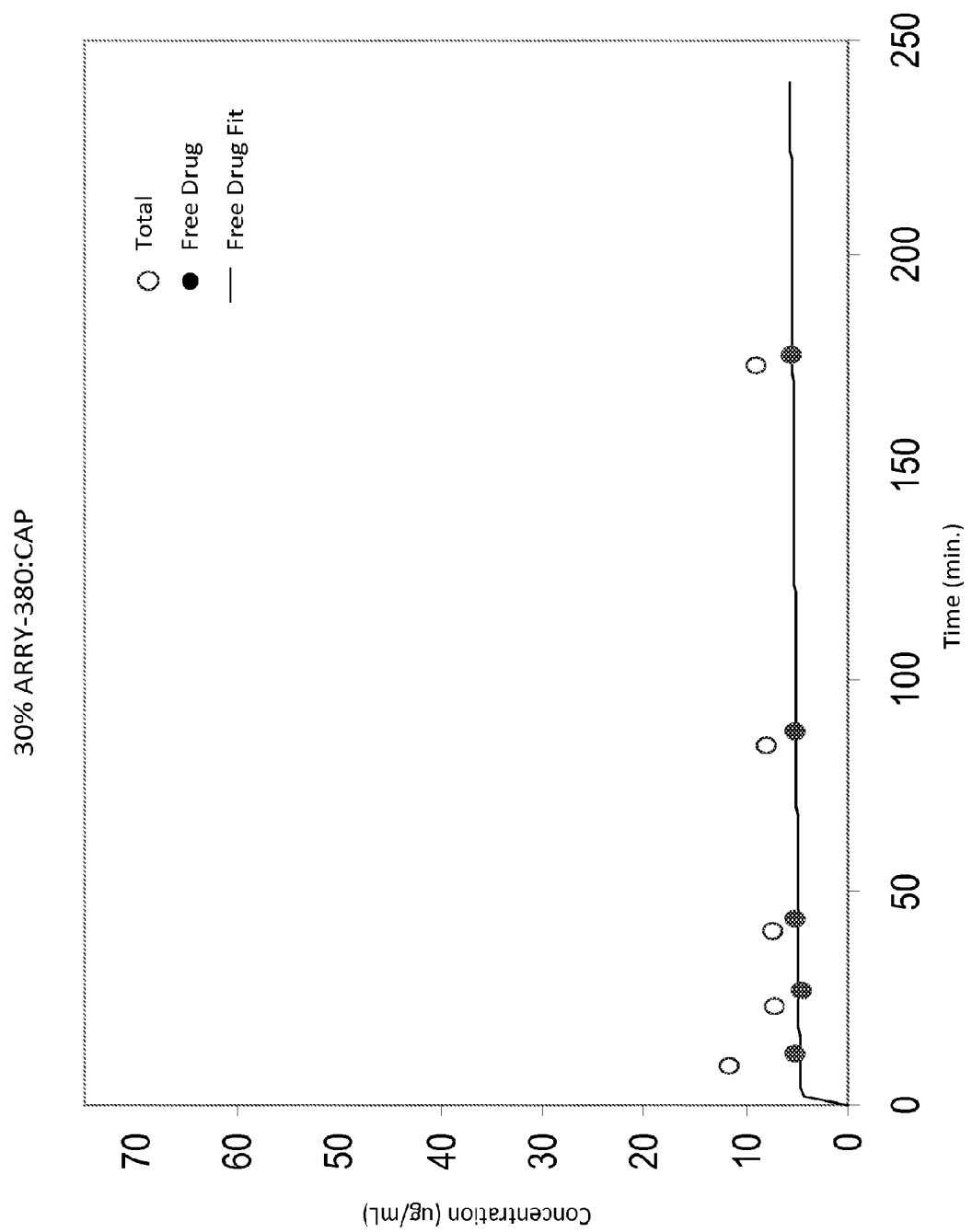
FIG. 5 shows a dissolution profile of a 30% solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

Dissolution testing was performed at a pH of 6.5 in phosphate buffer. The solid dispersion was suspended in H$_2$O and added directly to the buffer solution at 37° C. The dissolution profile was collected over a period of about 240 minutes. The results are in FIG. 5. The Cmax and AUC for the total drug species (colloidal+free) was 11.62 μg/mL and 36.69 μg/mL*hr, respectively. The Cmax and AUC for the free drug species was 5.64 μg/mL and 20.58 μg/mL*hr, respectively.

Example 5

30% Solid Dispersion using HPMCAS

A solid dispersion was prepared containing 30 weight percent N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and HPMCAS Grade M using a Buchi B-290 mini spray drier. The solid dispersion was spray dried from a MeOH:THF (1:3) solvent system, a 5% spray solution concentration, an inlet temperature of 80° C. at a flow rate of 35 mL/minute, drying gas flow rate of 40 m$^3$/hour, nozzle pressure of 80 psig, nozzle gas flow of 0.66 m$^3$/hour, and a 1.5 mm nozzle type. Secondary drying of the dispersion was done at 40° C. under vacuum for about 16 hours. The spray drying yielded 163.19 mg (48.3% yield) of the solid dispersion. Physicochemical analysis results are in Table 1. The XRPD scan is shown in FIG. 1. Residual solvent analysis showed that the dispersion had less than 0.5% THF and no detectable MeOH.

Figure 6:
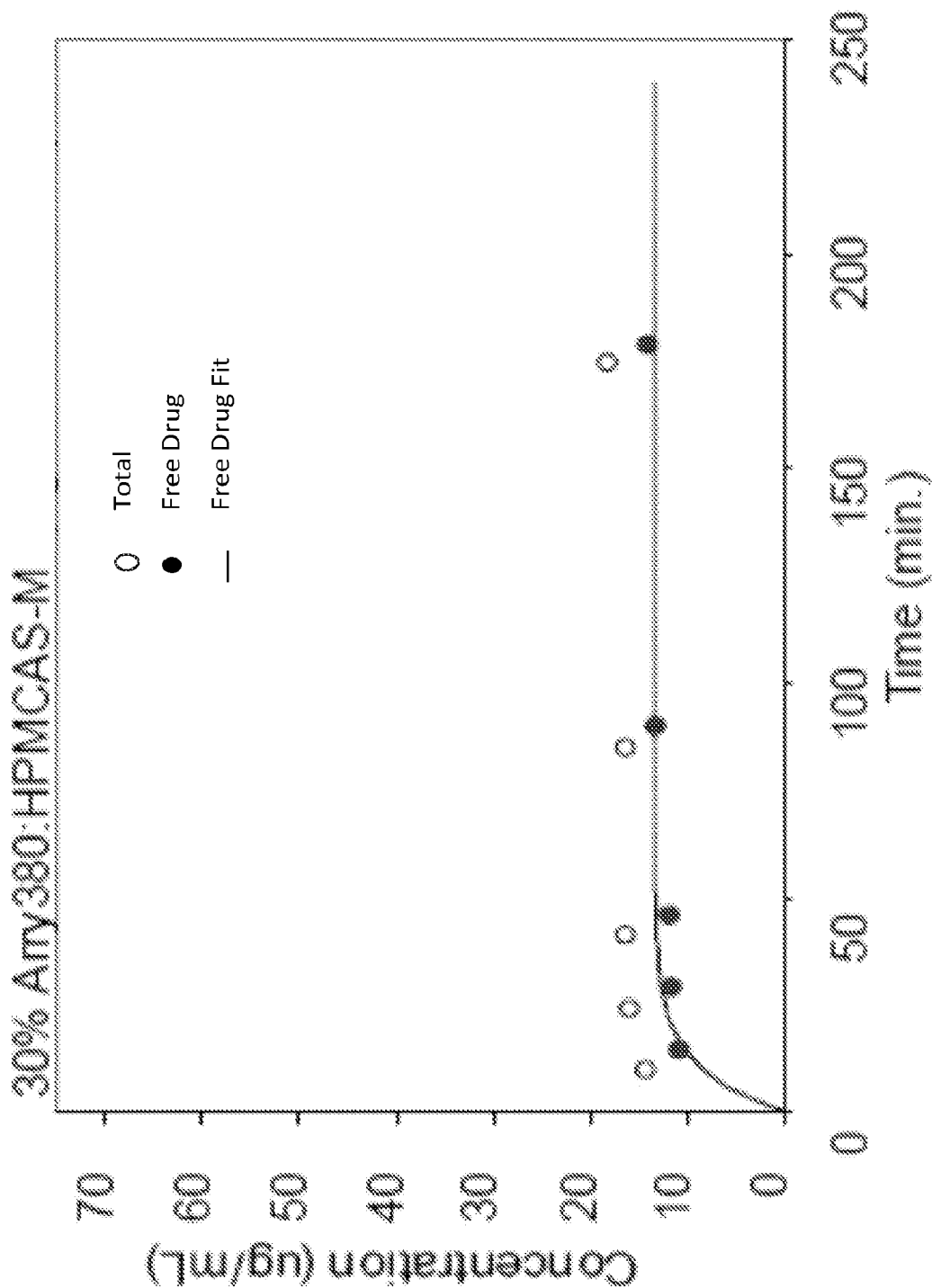
FIG. 6 shows a dissolution profile of a 30% solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

Dissolution testing was performed at a pH of 6.5 in phosphate buffer. The solid dispersion was suspended in H$_2$O and added directly to the buffer solution at 37° C. The dissolution profile was collected over a period of about 240 minutes. The results are in FIG. 6. The Cmax and AUC for the total drug species (colloidal+free) was 19.04 μg/mL and 68.09 μg/mL*hr, respectively. The Cmax and AUC for the free drug species was 13.50 μg/mL and 51.74 μg/mL*hr, respectively.

TABLE 1

| Example | Polymer | API:Polymer | HPLC (area %) | $T_g$ (° C.) | TGA wt loss (%) | % THF (w/w) | Hygroscopicity (% wt change at 80% RH) |
|---|---|---|---|---|---|---|---|
| REF |  |  | 99.39 |  | 4.9 |  | <1% |
| 1 | PVP-VA | 3:7 | 99.45 | 117 | 2.3 | 0.5 | 14.4 |
| 2 | Eudragit L100 | 3:7 | 98.63 | 116 | 5.9 | 4.5 | 7.5 |
| 3 | HPMCP H-55 | 3:7 | 97.30 | 149 | 1.7 | 0.3 | 7.5 |
| 4 | CAP | 3:7 | 95.45 | 179 | 1.9 | 0.5 | 7.8 |
| 5 | HPMCAS | 3:7 |  | 113 | NA | NA | NA |

Example 6

60% Solid Dispersion using PVP-VA

Figure 7:
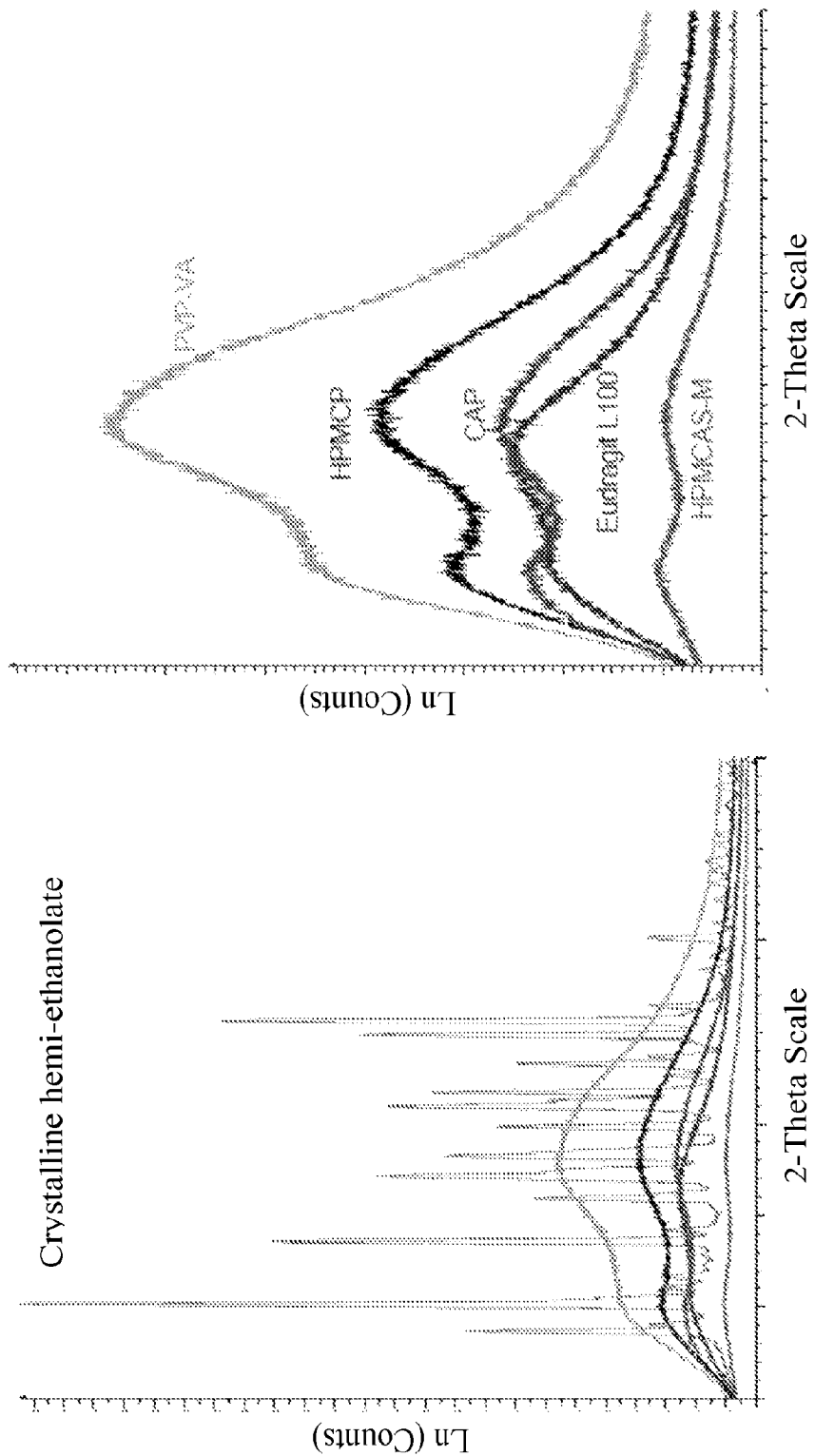
FIG. 7 shows a comparison of XRPD scans of amorphous 60% solid dispersions and crystalline N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine, with a close up of the amorphous solid dispersions.

A solid dispersion was prepared containing 60 weight percent N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and PVP-VA using a Buchi B-290 mini spray drier. The solid dispersion was spray dried from a MeOH:THF (1:3) solvent system, a 5% spray solution concentration, an inlet temperature of 80° C. at a flow rate of 35 mL/minute, drying gas flow rate of 40 m³/hour, nozzle pressure of 80 psig, nozzle gas flow of 0.66 m³/hour, and a 1.5 mm nozzle type. Secondary drying of the dispersion was done at 40° C. under vacuum for about 16 hours. The spray drying yielded 135.0 mg (88.2% yield) of the solid dispersion. The XRPD scan is shown in FIG. 7.

Figure 8:
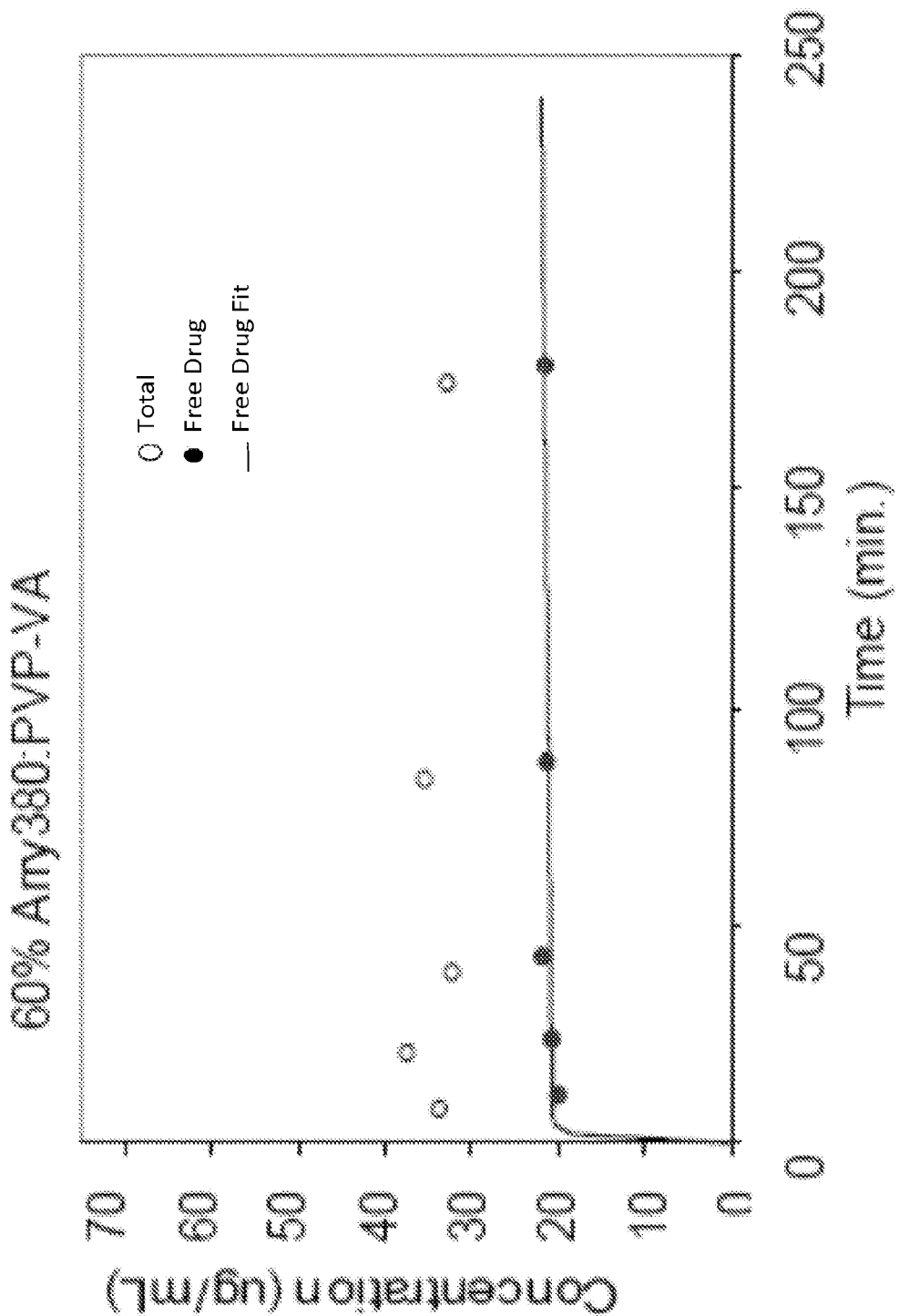
FIG. 8 shows a dissolution profile of a 60% solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

Dissolution testing was performed at a pH of 6.5 in phosphate buffer. The solid dispersion was suspended in H₂O and added directly to the buffer solution at 37° C. The dissolution profile was collected over a period of about 240 minutes. The results are in FIG. 8. The Cmax and AUC for the total drug species (colloidal+free) was 34.80 µg/mL and 133.76 µg/mL*hr, respectively. The Cmax and AUC for the free drug species was 21.88 µg/mL and 84.43 µg/mL*hr, respectively.

Example 7

60% Solid Dispersion using Eudragit

A solid dispersion was prepared containing 60 weight percent N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and Eudragit L100 using a Buchi B-290 mini spray drier. The solid dispersion was spray dried from a MeOH:THF (1:3) solvent system, a 5% spray solution concentration, an inlet temperature of 80° C. at a flow rate of 35 mL/minute, drying gas flow rate of 40 m³/hour, nozzle pressure of 80 psig, nozzle gas flow of 0.66 m³/hour, and a 1.5 mm nozzle type. Secondary drying of the dispersion was done at 40° C. under vacuum for about 16 hours. The spray drying yielded 88.1 mg (52.4% yield) of the solid dispersion. The XRPD scan is shown in FIG. 7.

Figure 9:
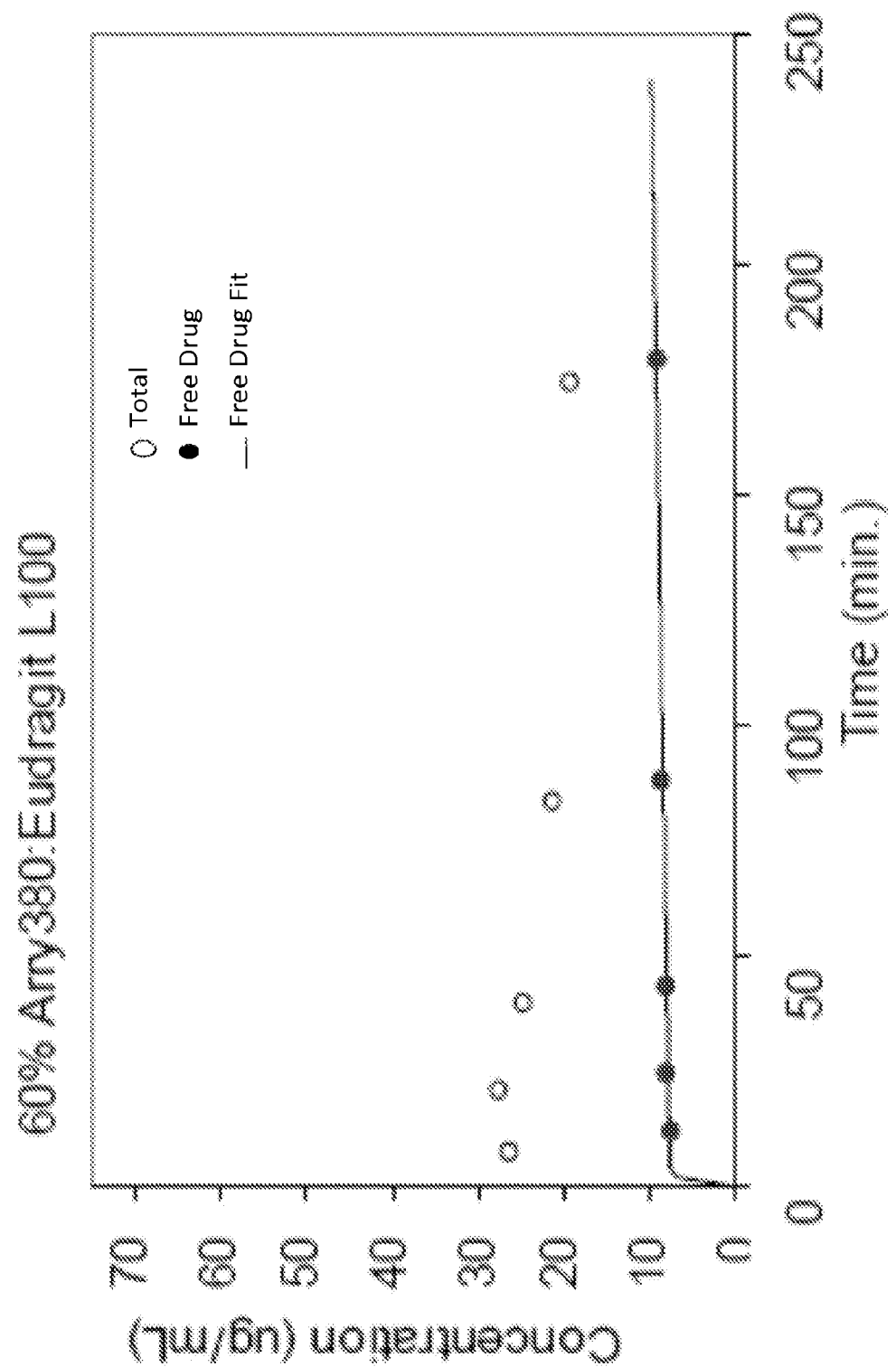
FIG. 9 shows a dissolution profile of a 60% solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

Dissolution testing was performed at a pH of 6.5 in phosphate buffer. The solid dispersion was suspended in H₂O and added directly to the buffer solution at 37° C. The dissolution profile was collected over a period of about 240 minutes. The results are in FIG. 9. The Cmax and AUC for the total drug species (colloidal+free) was 26.82 µg/mL and 84.49 µg/mL*hr, respectively. The Cmax and AUC for the free drug species was 9.85 µg/mL and 34.89 µg/mL*hr, respectively.

Example 8

60% Solid Dispersion using HPMCP

A solid dispersion was prepared containing 60 weight percent N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and HPMCP H-55 using a Buchi B-290 mini spray drier. The solid dispersion was spray dried from a MeOH:THF (1:3) solvent system, a 5% spray solution concentration, an inlet temperature of 80° C. at a flow rate of 35 mL/minute, drying gas flow rate of 40 m³/hour, nozzle pressure of 80 psig, nozzle gas flow of 0.66 m³/hour, and a 1.5 mm nozzle type. Secondary drying of the dispersion was done at 40° C. under vacuum for about 16 hours. The spray drying yielded 98.0 mg (58.0% yield) of the solid dispersion. The XRPD scan is shown in FIG. 7.

Figure 10:
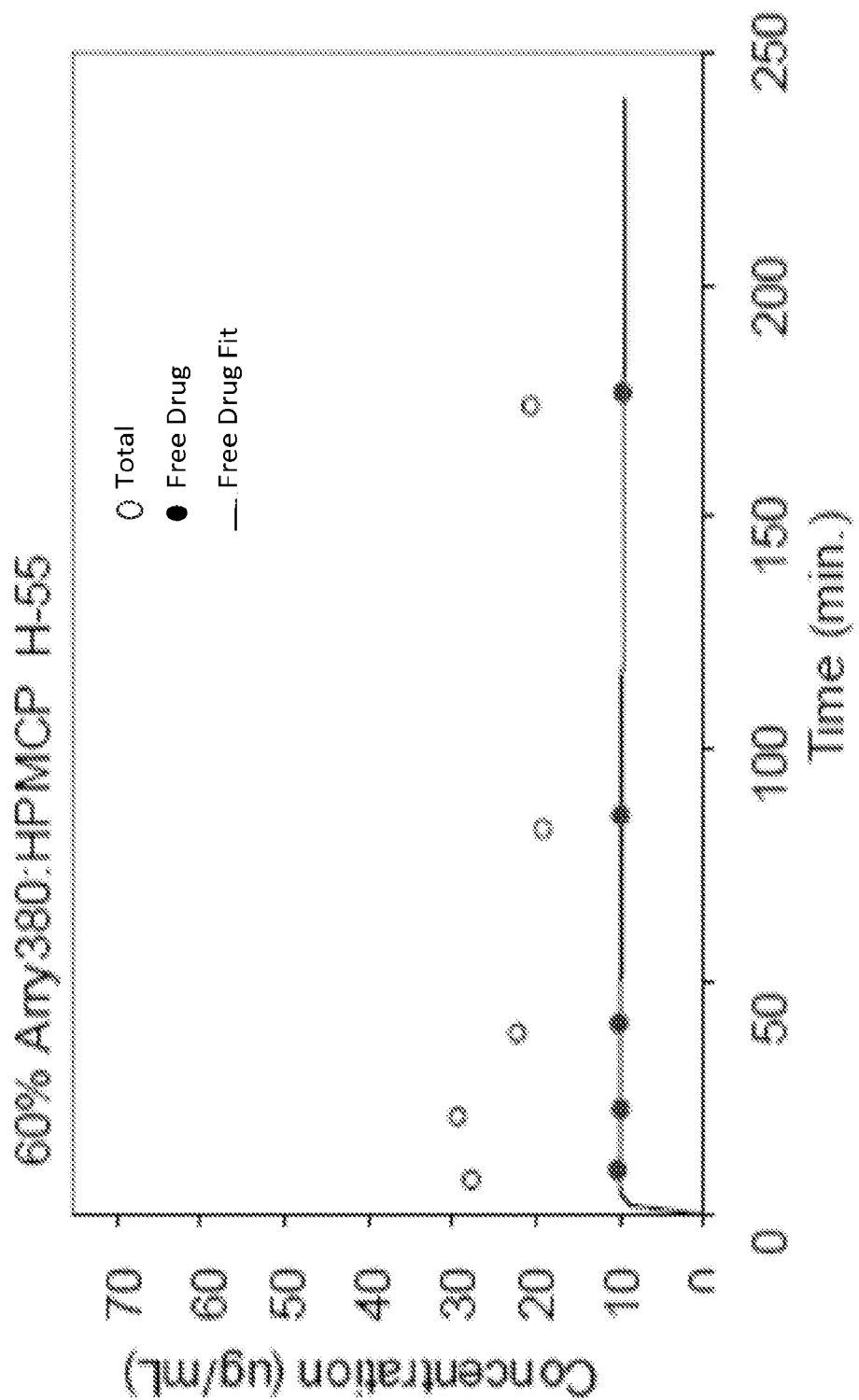
FIG. 10 shows a dissolution profile of a 60% solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

Dissolution testing was performed at a pH of 6.5 in phosphate buffer. The solid dispersion was suspended in H₂O and added directly to the buffer solution at 37° C. The dissolution profile was collected over a period of about 240 minutes. The results are in FIG. 10. The Cmax and AUC for the total drug species (colloidal+free) was 32.21 µg/mL and 38.28 µg/mL*hr, respectively. The Cmax and AUC for the free drug species was 9.96 µg/mL and 38.28 µg/mL*hr, respectively.

Example 9

60% Solid Dispersion using CAP

A solid dispersion was prepared containing 60 weight percent N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and CAP using a Buchi B-290 mini spray drier. The solid dispersion was spray dried from a MeOH:THF (1:3) solvent system, a 5% spray solution concentration, an inlet temperature of 80° C. at a flow rate of 35 mL/minute, drying gas flow rate of 40 m³/hour, nozzle pressure of 80 psig, nozzle gas flow of 0.66 m³/hour, and a 1.5 mm nozzle type. Secondary drying of the dispersion was done at 40° C. under vacuum for about 16 hours. The spray drying yielded 74.9 mg (44.6% yield) of the solid dispersion. The XRPD scan is shown in FIG. 7.

Figure 11:
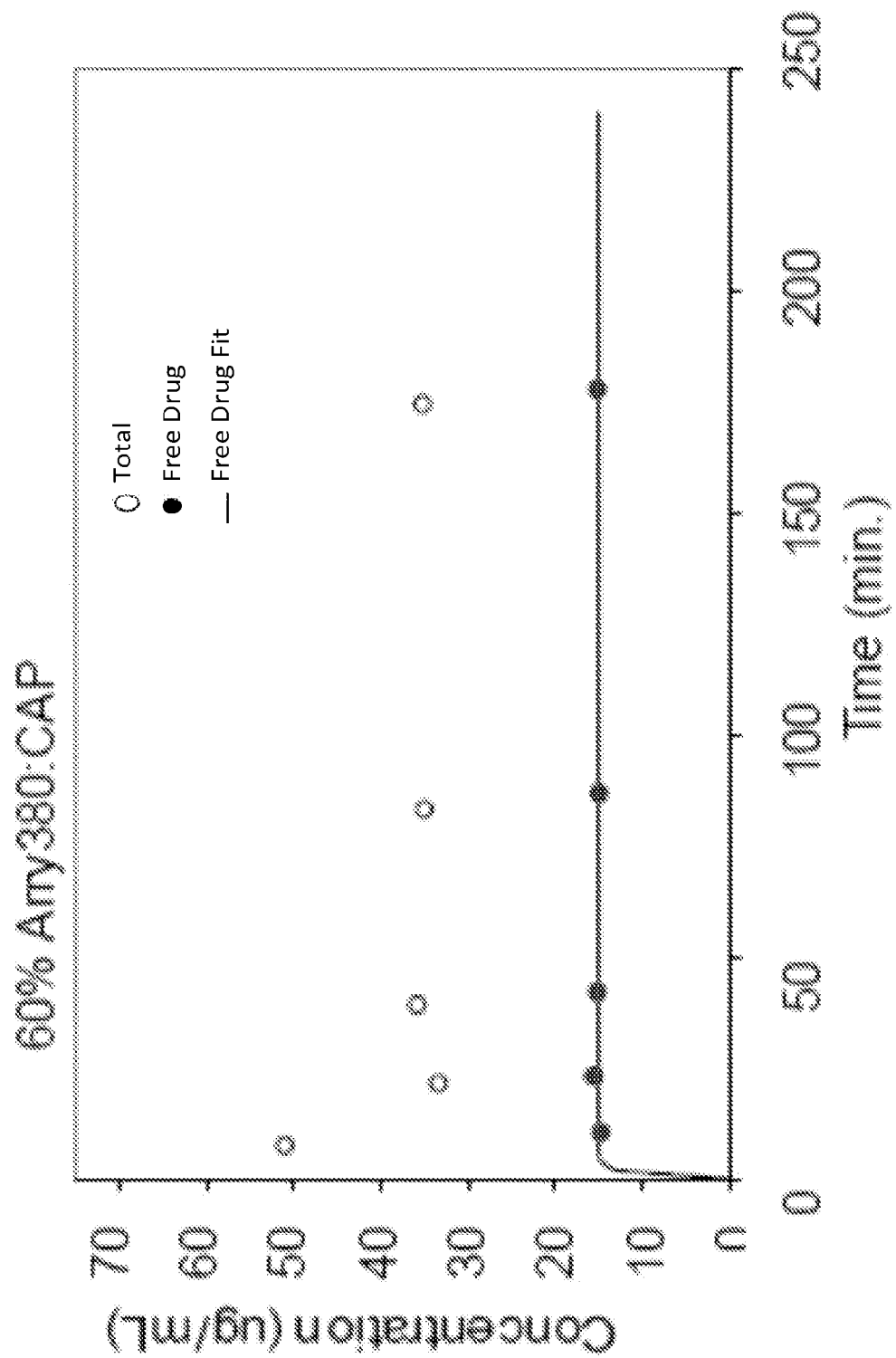
FIG. 11 shows a dissolution profile of a 60% solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

Dissolution testing was performed at a pH of 6.5 in phosphate buffer. The solid dispersion was suspended in H₂O and added directly to the buffer solution at 37° C. The dissolution profile was collected over a period of about 240 minutes. The results are in FIG. 11. The Cmax and AUC for the total drug species (colloidal+free) was 51.98 µg/mL and 144.91 µg/mL*hr, respectively. The Cmax and AUC for the free drug species was 15.07 µg/mL and 59.69 µg/mL*hr, respectively.

Example 10

60% Solid Dispersion using HPMCAS

A solid dispersion was prepared containing 60 weight percent N4-(4-([1,2,4]triazolo[1,5-α]pyridin-7-yloxy)-3-methylphenyl)-N6-(4,4-dimethyl-4,5-dihydrooxazol-2-yl) quinazoline-4,6-diamine and HPMCAS Grade M using a Buchi B-290 mini spray drier. The solid dispersion was spray dried from a MeOH:THF (1:3) solvent system, a 5% spray solution concentration, an inlet temperature of 80° C. at a flow rate of 35 mL/minute, drying gas flow rate of 40 m$^3$/hour, nozzle pressure of 80 psig, nozzle gas flow of 0.66 m$^3$/hour, and a 1.5 mm nozzle type. Secondary drying of the dispersion was done at 40° C. under vacuum for about 16 hours. The spray drying yielded 113.3 mg (67.2% yield) of the solid dispersion. The XRPD scan is shown in FIG. 7.

Figure 12:
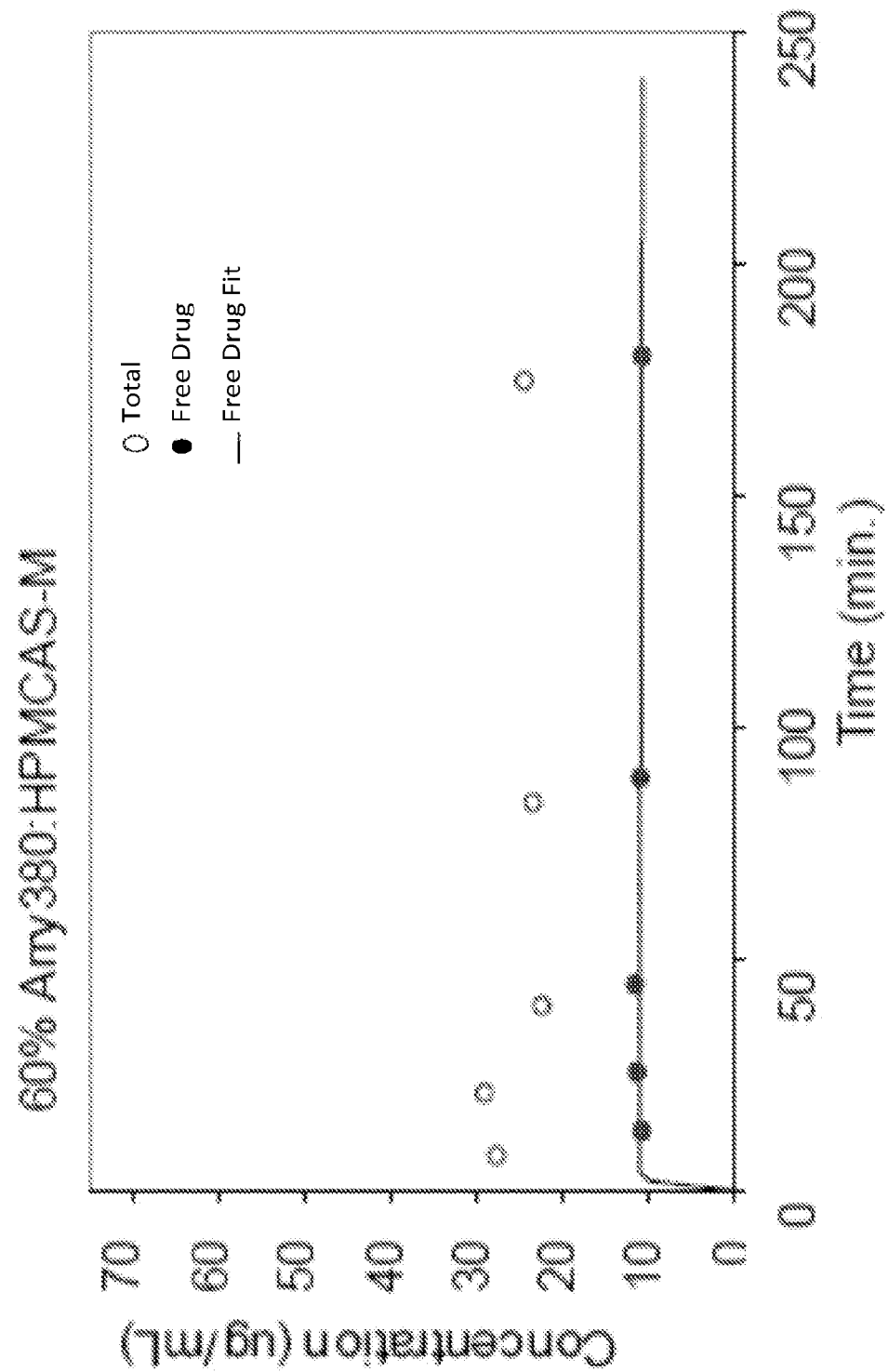
FIG. 12 shows a dissolution profile of a 60% solid dispersion of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine.

Dissolution testing was performed at a pH of 6.5 in phosphate buffer. The solid dispersion was suspended in H$_2$O and added directly to the buffer solution at 37° C. The dissolution profile was collected over a period of about 240 minutes. The results are in FIG. 12. The Cmax and AUC for the total drug species (colloidal+free) was 26.45 µg/mL and 96.21 µg/mL*hr, respectively. The Cmax and AUC for the free drug species was 10.96 µg/mL and 42.83 µg/mL*hr, respectively.

Example 11

50% Solid Dispersion using PVP-PA

A solid dispersion was prepared containing 50 weight percent N4-(4-([1,2,4]triazolo[1,5-α]pyridin-7-yloxy)-3-methylphenyl)-N6-(4,4-dimethyl-4,5-dihydrooxazol-2-yl) quinazoline-4,6-diamine and PVP-VA using a Buchi B-290 mini spray drier. The solid dispersion was spray dried from a MeOH:THF (1:3) solvent system, a 3.9% spray solution concentration, an inlet temperature of 100° C. at a flow rate of 30 mL/minute, drying gas flow rate of 40 m$^3$/hour, nozzle pressure of 80 psig, nozzle gas flow of 0.66 m$^3$/hour, and a 1.5 mm nozzle type. Secondary drying of the dispersion was done at 50° C. under vacuum for about 72 hours. The spray drying yielded 28.7 g (72.7% yield) of the solid dispersion.

Example 12

N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine freebase hemi-ethanolate Step 1: (E)-N'-(2-Cyano-4-(3-(1-hydroxy-2-methylpropan-2-yl)thioureido) phenyl)-N,N-dimethylformimidamide was coupled with 4-([1,2,4]triazolo[1,5α]pyridin-7-yloxy)-3-methylaniline in isopropyl acetate:acetic acid (65:35 v/v) at 45° C. to yield 1-(4-((4-([1,2,4]triazolo[1,5-α]pyridin-7-yloxy)-3-methylphenyl)amino)quinazolin-6-yl)-3-(1-hydroxy-2-methylpropan-2-yl)thiourea (91%).

Step 2: 1-(4-((4-([1,2,4]Triazolo[1,5-α]pyridin-7-yloxy)-3-methylphenyl)amino)quinazolin-6-yl)-3-(1-hydroxy-2-methylpropan-2-yl)thiourea was agitated in tetrahydrofuran under basic conditions (2.5N NaOH), followed by the addition of p-toluenesulfonyl chloride. Water was charged to yield N4-(4-([1,2,4]triazolo[1,5-α]pyridin-7-yloxy)-3-methylphenyl)-N6-(4,4-dimethyl-4,5-dihydrooxazol-2-yl) quinazoline-4,6-diamine (96%) as a mixture of polymorphs (generally a mixture containing one or more of Form C, Form G hemi-THF, Form G mono-THF, Form M or Form P).

Step 3: N4-(4-([1,2,4]Triazolo[1,5-α]pyridin-7-yloxy)-3-methylphenyl)-N6-(4,4-dimethyl-4,5-dihydrooxazol-2-yl) quinazoline-4,6-diamine from Step 2 was triturated in ethanol at greater than 65° C. to provide N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine Form B Ethanol (89%).

The crystalline hemi-ethanolate (Form B Ethanol) XRPD scans are shown in FIGS. 1 and 7.

Dissolution testing was performed at a pH of 6.5 in phosphate buffer. The crystals (particles) were suspended in H$_2$O and added directly to the buffer solution at 37° C. The dissolution profile was collected over a period of about 240 minutes. The Cmax and AUC for the free drug species was 0.44 µg/mL and 5.49 µg/mL*hr, respectively.

Example 13

Pharmaceutical Composition 1

Tablets containing the solid dispersions of any of Examples 1 to 11 may be prepared in a conventional manner comprising:

| Function | Ingredient | % of Blend |
| --- | --- | --- |
| API | Solid dispersion as prepared in Example 11 | 50 |
| Disintegrant | Crospovidone - Polyplasdone ® | 6 |
| Osmogen | NaCl | 5 |
| Osmogen | KCl | 5 |
| Glidant | Colloidal Silicon Dioxide | 0.5 |
| Lubricant Extragranular | Magnesium Stearate | 0.25 |
| Binder/Diluent | Microcrystalline cellulose - Avicel ® | 19.25 |
| Osmogen | NaCl | 4.625 |
| Osmogen | KCl | 4.625 |
| Disintegrant | Polyplasdone | 4 |
| Glidant | Colloidal Silicon Dioxide | 0.5 |
| Lubricant | Magnesium Stearate | 0.25 |

In one preparation, tablets were made using OPADRY II 85F92727 at 3% by weight as a tablet coating. The tablets contained 150 mg of API.

Example 14

Pharmaceutical Composition 2

Tablets containing the solid dispersions of any of Examples 1 to 11 may be prepared in a conventional manner comprising:

| Function | Ingredient | % of Blend |
| --- | --- | --- |
| API | Solid dispersion as prepared in Example 11 | 50 |
| Disintegrant | Crospovidone - Polyplasdone ® | 6 |

-continued

| Function | Ingredient | % of Blend |
|---|---|---|
| Disintegrant | NaHCO$_3$ | 3 |
| Osmogen | NaCl | 5 |
| Osmogen | KCl | 5 |
| Glidant | Colloidal Silicon Dioxide | 0.5 |
| Lubricant Extragranular | Magnesium Stearate | 0.25 |
| Binder/Diluent | Microcrystalline cellulose - Avicel ® | 16.25 |
| Osmogen | NaCl | 4.625 |
| Osmogen | KCl | 4.625 |
| Disintegrant | Polyplasdone | 4 |
| Glidant | Colloidal Silicon Dioxide | 0.5 |
| Lubricant | Magnesium Stearate | 0.25 |

In one preparation, tablets were made using OPADRY II 85F92727 at 3% by weight as a tablet coating. The tablets contained 150 mg of API.

Example 15

Pharmaceutical Composition 3

Tablets containing the solid dispersions of any of Examples 1 to 11 may be prepared in a conventional manner comprising:

| Function | Ingredient | % of Blend |
|---|---|---|
| API | Solid dispersion as prepared in Example 11 | 50 |
| Disintegrant | Crospovidone - Polyplasdone ® | 6 |
| Osmogen | NaCl | 10.625 |
| Osmogen | KCl | 10.625 |
| Filler | Lactose | 21.25 |
| Glidant | Colloidal Silicon Dioxide | 0.5 |
| Lubricant Extragranular | Magnesium Stearate | 0.25 |
| Glidant | Colloidal Silicon Dioxide | 0.5 |
| Lubricant | Magnesium Stearate | 0.25 |

In one preparation, tablets were made using OPADRY II 85F92727 at 3% by weight as a tablet coating. The tablets contained 150 mg of API.

Example 16

Referential Pharmaceutical Composition—Powder-in-Capsule

A PIC composition was prepared containing 25 mg or 100 mg of N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine as prepared in Example 12. The PIC composition was prepared in size 00 white opaque hard gelatin capsules.

Figure 13:
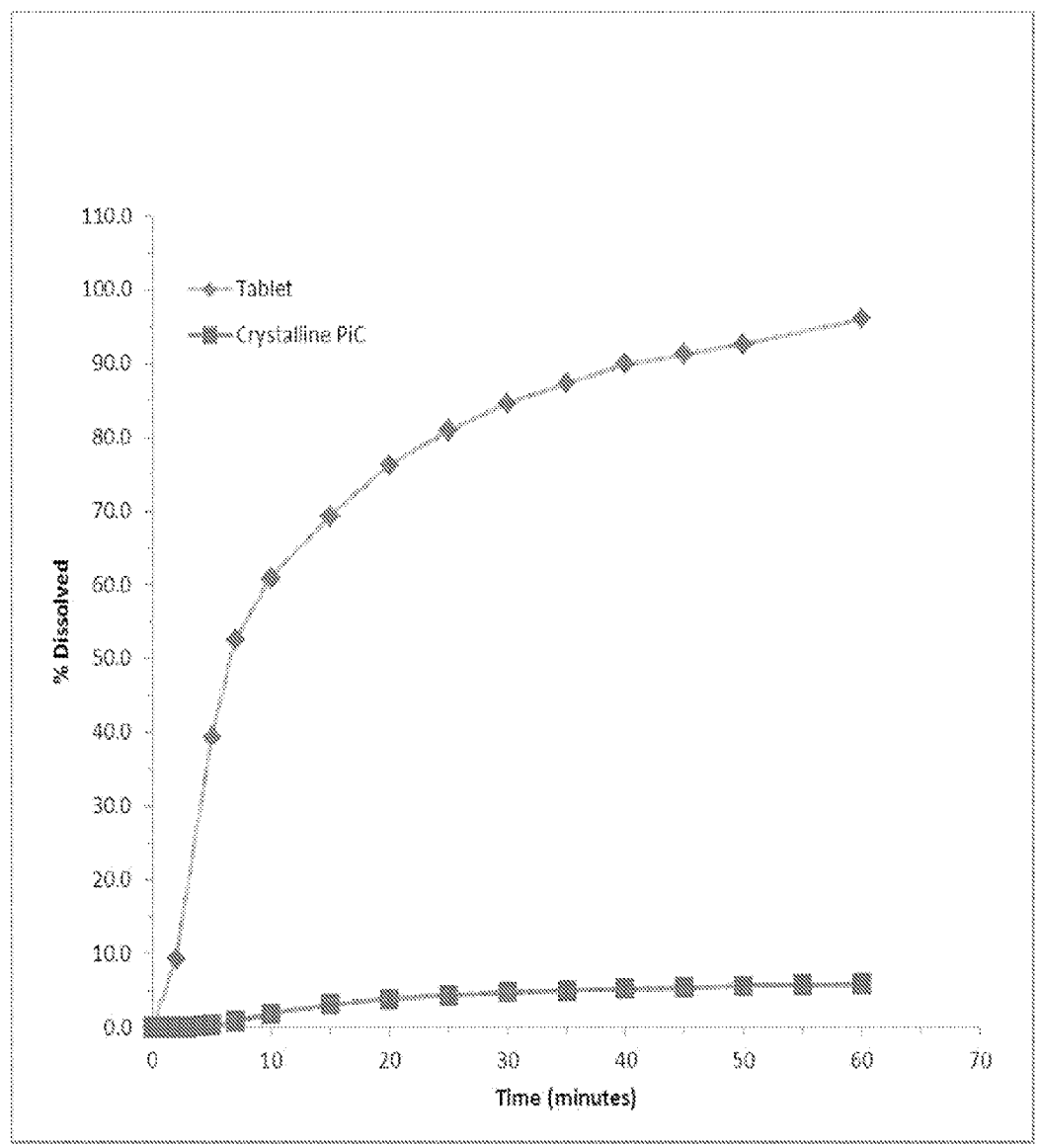
FIG. 13 shows a dissolution comparison of a solid dispersion tablet and a crystalline PIC composition.

A dissolution test comparison was performed comparing the crystalline hemi-ethanolate PIC composition of Example 16 and the 50% PVP-VA solid dispersion (Example 11) tablet of Example 13 in 900 mL of 10 mM citrate buffer at 37° C. and a pH of 4.5, using USP Apparatus II at 75 rpm. The results are shown in FIG. 13.

Example 17

Stability Screen

A stability screen of the spray dried dispersions was completed at 40° C., 75% relative humidity under open conditions, in glass vials, over a period of 8 days. Results are shown in TABLE 2.

TABLE 2

| | HPLC Area % | | | |
|---|---|---|---|---|
| Time | Example 1 | Example 2 | Example 3 | Example 4 |
| Standard | 99.39 | 99.39 | 99.39 | 99.39 |
| As received | 99.45 | 98.63 | 97.30 | 95.45 |
| 4 days | 99.21 | 96.10 | 93.03 | 90.89 |
| 8 days | 99.35 | 93.16 | 86.63 | 87.15 |

The main degradant observed was the carbamate impurity, likely due to the acidic nature of some of these polymers. XRPD analysis over the course of the study showed no evidence of crystallization for any solid dispersion of Examples 1-4.

Example 18

In Vivo Pharmacokinetics in Beagles

The solid dispersion of Example 1 was tested against a crystalline, micronized suspension formulation (d(v, 0.9)=3.0 μm) of Example 12 under normal fasted conditions, as well as with pretreatment using pentagastrin or famotidine. The solid dispersion of Example 1 was prepared as a suspension in water and administered orally. The micronized suspension of Example 12 was prepared as a suspension with SyrSpend® SF Dry reconstituted with water and administered orally. To reduce variability, beagles were crossed over from pentagastrin to famotidine after a 5 day washout period. Pentagastrin is a pH modifier to modify gastric pH to about 2 to 3, and famotidine is a pH modifier to modify gastric pH to about 5 to 7.5 (Zhou, Rong, et al. "pH-Dependent Dissolution in Vitro and Absorption in Vivo of Weakly Basic Drugs Development of a Canine Model." *Pharm. Res*. Vol. 22, No. 2 (February 2005): pp. 188-192). There were four beagles per group. Group A received pentagastrin pretreatment, the micronized suspension of Example 12, followed by a 5 day washout period, then famotidine pretreatment, and finally the micronized suspension of Example 12. Group B received pentagastrin pretreatment, the solid dispersion of Example 1, followed by a 5 day washout period, then famotidine pretreatment, and finally the solid dispersion of Example 1. Group C received the micronized suspension of Example 12, followed by a 5 day washout period, and finally the solid dispersion of Example 1. Results are shown in TABLE 3.

TABLE 3

| Pretreatment | Dosing Formulation | AUC$_{inf}$ (μg*hr/mL) | C$_{max}$ (μg/mL) |
|---|---|---|---|
| None | Micronized Suspension of Example 12 | 7.43 ± 1.77 | 1.88 ± 0.35 |
| | Solid Dispersion of Example 1 | 10.0 ± 2.7 | 2.29 ± 0.54 |
| 6 μg/kg Pentagastrin | Micronized Suspension of Example 12 | 17.2 ± 2.7 | 3.29 ± 0.13 |
| | Solid Dispersion of Example 1 | 13.0 ± 3.6 | 3.12 ± 0.62 |

TABLE 3-continued

| Pretreatment | Dosing Formulation | AUC$_{inf}$ (μg*hr/mL) | C$_{max}$ (μg/mL) |
|---|---|---|---|
| 40 mg/kg Famotidine | Micronized Suspension of Example 12 | 1.74 ± 0.39 | 0.514 ± 0.092 |
| | Solid Dispersion of Example 1 | 6.32 ± 2.88 | 1.45 ± 0.54 |

It will be understood that the enumerated embodiments are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A solid dispersion comprising amorphous N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine and a dispersion polymer, wherein the dispersion polymer is PVP-VA.

2. The solid dispersion of claim 1, wherein the N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine is present in an amount of from about 0.1% to about 50% by weight relative to the dispersion polymer.

3. The solid dispersion of claim 1, wherein the N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine is present in an amount of from about 5% to about 35% by weight relative to the dispersion polymer.

4. The solid dispersion of claim 1, wherein the N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine is present in an amount of from about 25% to about 35% by weight relative to the dispersion polymer.

5. The solid dispersion of claim 1, wherein at least 80% of the N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine is in amorphous form.

6. The solid dispersion of claim 1, wherein at least 95% of the N4-(4-([1,2,4]triazolo[1,5-α]pyridin-7-yloxy)-3-methylphenyl)-N6-(4,4-dimethyl-4,5-dihydrooxazol-2-yl)quinazoline-4,6-diamine is in amorphous form.

7. A pharmaceutical composition comprising a solid dispersion according to claim 1 and one or more pharmaceutically acceptable excipients.

8. The pharmaceutical composition of claim 7, wherein the composition is a tablet.

9. A pharmaceutical composition comprising:
(a) about 1 to about 70 weight % of the solid dispersion of claim 1;
(b) about 0.1 to 20 weight % of a disintegrant;
(c) about 0.1 to 25 weight % of an osmogen;
(d) about 0.1 to 10 weight % of a glidant;
(e) about 0.1 to 10 weight % of a lubricant; and
(f) about 0.1 to 25 weight % of a binder.

10. A pharmaceutical composition comprising:
(a) about 1 to about 70 weight % of the solid dispersion of claim 1;
(b) about 0.1 to 20 weight % of a disintegrant;
(c) about 0.1 to 25 weight % of an osmogen;
(d) about 0.1 to 10 weight % of a glidant;
(e) about 0.1 to 10 weight % of a lubricant; and
(f) about 0.1 to 25 weight % of a filler.

11. The pharmaceutical composition of claim 9, wherein the binder is about 10 to 25 weight %.

12. The pharmaceutical composition of claim 9, wherein the disintegrant is about 5 to 15 weight %.

13. The pharmaceutical composition of claim 10, wherein the filler is about 10 to 25 weight %.

14. The pharmaceutical composition of claim 9, wherein the disintegrant is about 1 to 10 weight %.

15. The pharmaceutical composition of claim 9, wherein the osmogen is about 15 to 25 weight %.

16. The pharmaceutical composition of claim 9, wherein the glidant is about 0.1 to 3 weight %.

17. The pharmaceutical composition of claim 9, wherein the lubricant is about 0.1 to 3 weight %.

18. A pharmaceutical composition comprising:
(a) solid dispersion of claim 1; and
(b) sodium bicarbonate.

19. A pharmaceutical composition comprising:
(a) about 1 to about 70 weight % of the solid dispersion of claim 1; and
(b) about 0.1 to about 30 weight % sodium bicarbonate.

20. The pharmaceutical composition of claim 9, wherein the solid dispersion is about 25 to about 60 weight %.

21. The pharmaceutical composition of claim 9, wherein the solid dispersion is about 40 to about 60 weight %.

22. The pharmaceutical composition of claim 9, wherein the composition is a tablet.

23. A method for the treatment of ErbB2 positive breast cancer comprising administering to a patient in need thereof a therapeutically effective amount of the solid dispersion of claim 1.

24. A process of preparing the solid dispersion of claim 1 comprising the steps of:
(a) dissolving N4-(4-(1,2,4]triazolo[1,5-α]pyridine-7-yloxy)-3-methylphenyl)-N6-(4,4-dimethyl-4,5-dihydrooxazol-2-yl)quinazoline-4,6-diamine and the dispersion polymer in a suitable solvent to form a feed solution; and
(b) evaporating the solvent by spray drying the feed solution to form the solid dispersion.

* * * * *